United States Patent
Kwon et al.

(10) Patent No.: US 9,399,284 B2
(45) Date of Patent: Jul. 26, 2016

(54) ROBOT CLEANER AND CONTROL METHOD THEREOF

(71) Applicant: SAMSUNG ELECTRONICS CO., LTD., Suwon-si (KR)

(72) Inventors: Joonhyung Kwon, Seoul (KR); Shin Kim, Hwaseong-si (KR); Ji Won Chun, Yongin-si (KR)

(73) Assignee: SAMSUNG ELECTRONICS CO., LTD., Suwon-Si (KR)

( * ) Notice: Subject to any disclaimer, the term of this patent is extended or adjusted under 35 U.S.C. 154(b) by 83 days.

(21) Appl. No.: 14/164,595

(22) Filed: Jan. 27, 2014

(65) Prior Publication Data

US 2014/0214205 A1 Jul. 31, 2014

(30) Foreign Application Priority Data

Jan. 29, 2013 (KR) .................. 10-2013-0009579

(51) Int. Cl.
| | | |
|---|---|---|
| *B25J 9/00* | (2006.01) | |
| *A47L 9/28* | (2006.01) | |
| *A47L 11/40* | (2006.01) | |
| *G01N 29/11* | (2006.01) | |
| *G05D 1/02* | (2006.01) | |

(52) U.S. Cl.
CPC .............. *B25J 9/0003* (2013.01); *A47L 9/2826* (2013.01); *A47L 11/4011* (2013.01); *G01N 29/11* (2013.01); *G05D 1/0255* (2013.01); *A47L 2201/04* (2013.01); *A47L 2201/06* (2013.01); *G01N 2291/044* (2013.01); *G01N 2291/2632* (2013.01); *G05D 2201/0215* (2013.01)

(58) Field of Classification Search
CPC ...... B25J 9/0003; B25J 9/163; B25J 11/0085; B25J 11/08; B25J 11/086; B25J 19/026; B25J 19/027; B25J 19/028; A47L 11/4011; A47L 2201/00; A47L 2201/04; A47L 2201/06; A47L 9/2826; G05D 2201/0215; G05B 2219/37024; G05B 2219/37032; G05B 2219/39354

See application file for complete search history.

(56) References Cited

U.S. PATENT DOCUMENTS

2003/0193267 A1* 10/2003 Mueller ........................ 310/328
2005/0065662 A1*  3/2005 Reindle et al. .................... 701/1

(Continued)

FOREIGN PATENT DOCUMENTS

DE   10 2007 025389 A1   12/2008
EP      0 474 542 A2      3/1992

(Continued)

OTHER PUBLICATIONS

European Search Report dated Aug. 25, 2015 issued in corresponding European Patent Application 14152714.3.

*Primary Examiner* — James Trammell
*Assistant Examiner* — Adam Mott
(74) *Attorney, Agent, or Firm* — Staas & Halsey LLP

(57) ABSTRACT

A robot cleaner includes a main body, a traveling unit installed in the main body, to move the main body, an ultrasonic sensor to emit an oscillation wave, to receive a reflection wave reflected from an object surface, and to output vibration generated by the oscillation wave and vibration generated by the reception of the reflection wave as an electrical signal, a waveform analyzer to calculate a generation time period of the electrical signal output from the ultrasonic sensor, and a controller to determine information about the object surface based on the calculated generation time period of the electrical signal, and to control movement of the traveling unit based on the information about the object surface.

26 Claims, 25 Drawing Sheets

(56) References Cited

U.S. PATENT DOCUMENTS

2008/0039974 A1* 2/2008 Sandin et al. ............... 700/258
2009/0266165 A1* 10/2009 Greenwood ................. 73/597

FOREIGN PATENT DOCUMENTS

| EP | 1 136 027 A2 | 9/2001 |
| WO | 2005/083541 A1 | 9/2005 |

* cited by examiner

ROBOT CLEANER AND CONTROL METHOD THEREOF

CROSS-REFERENCE TO RELATED APPLICATIONS

This application claims the benefit of Korean Patent Application No. 10-2013-0009579, filed on Jan. 29, 2013 in the Korean Intellectual Property Office, the disclosure of which is incorporated herein by reference.

BACKGROUND

1. Field

Embodiments of the present disclosure relate to a robot cleaner to acquire information about the surface of an object and to control operation based on the acquired information, and a control method thereof.

2. Description of the Related Art

Lately, with developments in electronic technology, such as computing technology, sensing technology, and communication technology, technology for automating human tasks in specific environments is rapidly advancing.

Accordingly, studies into autonomous mobile devices that autonomously travel without user manipulation are being actively conducted. The autonomous mobile devices include an industrial robot, a domestic robot, a service robot, and a security robot, all of which perform human tasks and offer various kinds of convenience for humans.

Also, in order to improve the traveling performance of the autonomous mobile devices, technology for building a map of a target area and for recognizing a location, technology for detecting obstacles, stair gaps, and the like and avoiding the obstacles, etc. are being actively developed.

Since the traveling performance of an autonomous mobile device depends on the composition and condition of a floor, technology for acquiring information about a floor surface, such as the material of the floor surface or the contaminated state of the floor surface, is needed.

A robot cleaner, which is a type of a domestic robot, can clean a floor such as a wooden floor with an appropriate suction force even without taking the material or condition of the floor surface into consideration. When the robot cleaner cleans a carpet, however, it may not clean the carpet appropriately since wheels often get stuck into the carpet or a brush fails to smoothly move. In other words, since the traveling performance and functions of the robot cleaner depend on the material, condition, etc. of a floor surface, technology for detecting the state of a floor surface is demanded.

Generally, the robot cleaner detects the surface state of a floor based on data sensed by an ultrasonic sensor or an infrared sensor.

The ultrasonic sensor calculates a distance to a floor using velocity at which ultrasonic waves are transmitted in the air. In the case of using the ultrasonic sensor, there is a problem that it is difficult to accurately distinguish materials of various types of objects since a floor material is determined only using the intensity of a reflected ultrasonic wave. Also, when the ultrasonic sensor is used at a short distance to a floor, the ultrasonic sensor may fail to properly operate due to composite waves.

The infrared sensor measures an amount of radiation from emitted light. The infrared sensor has a simple structure, and can be fabricated at low cost, compared to Position Sensing Device (PSD) sensors. However, optical members included in the infrared sensor are vulnerable to scratches, contaminants such as dust, etc. Moreover, cleaning the surface of the infrared sensor is not easy, and the infrared sensor may operate incorrectly when it is exposed to hard light. For these reasons, it is difficult to maintain and manage the infrared sensor. Furthermore, the infrared sensor has relatively low accuracy in detecting the surface condition of a floor.

SUMMARY

Therefore, it is an aspect of the present disclosure to provide a robot cleaner for acquiring information about the surface of an object, such as a composition or material of the object surface, whether the object surface has been contaminated by liquid, whether an empty space exists, etc., by analyzing the waveform of at least one wave among an oscillation wave, a reflection wave, and a composite wave, as well as the intensity of an ultrasonic wave, and for traveling while avoiding specific objects/areas based on the acquired information about the object surface, and a control method of the robot cleaner.

It is another aspect of the present disclosure to provide a robot cleaner for acquiring information about the surface of an object using composite waves respectively detected by a plurality of ultrasonic sensors installed at different distances to the object surface, and a control method of the robot cleaner.

Additional aspects of the disclosure will be set forth in part in the description which follows and, in part, will be obvious from the description, or may be learned by practice of the disclosure.

In accordance with one aspect of the present disclosure, a robot cleaner includes: a main body; a traveling unit installed in the main body and moving the main body; a ultrasonic sensor emitting an oscillation wave, receiving a reflection wave reflected from an object, and outputting vibration generated by the oscillation wave and vibration generated by the reception of the reflection wave as an electrical signal; and a controller determining information about the object surface based on the electrical signal output from the ultrasonic sensor, and controlling movement of the traveling unit based on the information about the object surface.

In accordance with another aspect of the present disclosure, a method of controlling a robot cleaner includes: driving an ultrasonic sensor to emit an oscillation wave; receiving a reflection wave reflected from an object through the ultrasonic sensor; detecting an electrical signal if vibration generated by the oscillation wave and vibration generated by the reflection wave reflected from the object are output as the electrical signal from the ultrasonic sensor; determining information about the object surface based on the electrical signal; and controlling movement of a traveling unit based on the information about the object surface.

In accordance with another aspect of the present disclosure, a robot cleaner includes an ultrasonic sensor to emit an oscillation wave, to receive a reflection wave reflected from a floor, and to output a signal generated from the oscillation wave and from the reception of the reflection wave and a controller to determine information about the floor based on the electrical signal output from the ultrasonic sensor.

In accordance with another aspect of the present disclosure, a robot cleaner includes a first ultrasonic sensor to acquire information about the floor surface, the first ultrasonic sensor being disposed on the robot cleaner a first distance above the floor and a second ultrasonic sensor to acquire information about the floor surface, the second ultrasonic sensor being disposed on the robot cleaner a second distance above the floor surface. The first distance is different than the second difference.

In the robot cleaner, a difference between the first distance and the second distance may be predetermined to correspond to a quarter of a wavelength at which the first and second ultrasonic sensors emit radiation.

In accordance with another aspect of the present disclosure, a robot cleaner includes: a main body; a traveling unit installed in the main body, and moving the main body; an ultrasonic sensor emitting an oscillation wave, receiving a reflection wave reflected from an object, and outputting vibration generated by the oscillation wave and vibration generated by the reception of the reflection wave as an electrical signal; a waveform analyzer calculating a generation time period of the electrical signal output from the ultrasonic sensor; and a controller determining information about the object surface based on the calculated generation time period of the electrical signal, and controlling movement of the traveling unit based on the information about the object surface.

Therefore, according to the aspects as described above, by analyzing the waveforms of an oscillation wave, a reflection wave, and a composite wave as well as the intensity of an ultrasonic wave, it is possible to acquire accurate information about the surface of an object, including basic information about the object such as the location of the object, information about the mechanical properties of the object, such as a material of the object, a surface shape of the object, a degree of elasticity of the object, etc., whether the object has been contaminated by liquid, etc., and by controlling the operation of the robot cleaner based on the information about the object surface, the operation of the robot cleaner may be effectively controlled.

Also, by using an ultrasonic sensor of a closed, watertight structure having excellent fouling resistant and high durability rather than an optical sensor such as an infrared sensor, it is possible to clean the ultrasonic sensor when it was contaminated, to prevent an emitted ultrasonic wave from attenuating, and also to increase reception sensitivity.

Also, since accuracy of information about a floor surface is improved so that the robot cleaner can decide a traveling direction and automatically set a cleaning mode based on the information about the floor surface, the efficiency of cleaning may be improved, resulting in high consumer satisfaction.

In addition, by combining information about a floor surface acquired by the ultrasonic sensor with optical information and image information, it is possible to improve discrimination of information about the shape and location of an obstacle so that the operation and functions of the robot cleaner can be precisely controlled.

BRIEF DESCRIPTION OF THE DRAWINGS

These and/or other aspects of the disclosure will become apparent and more readily appreciated from the following description of embodiments, taken in conjunction with the accompanying drawings of which.

DETAILED DESCRIPTION

Figure 1:
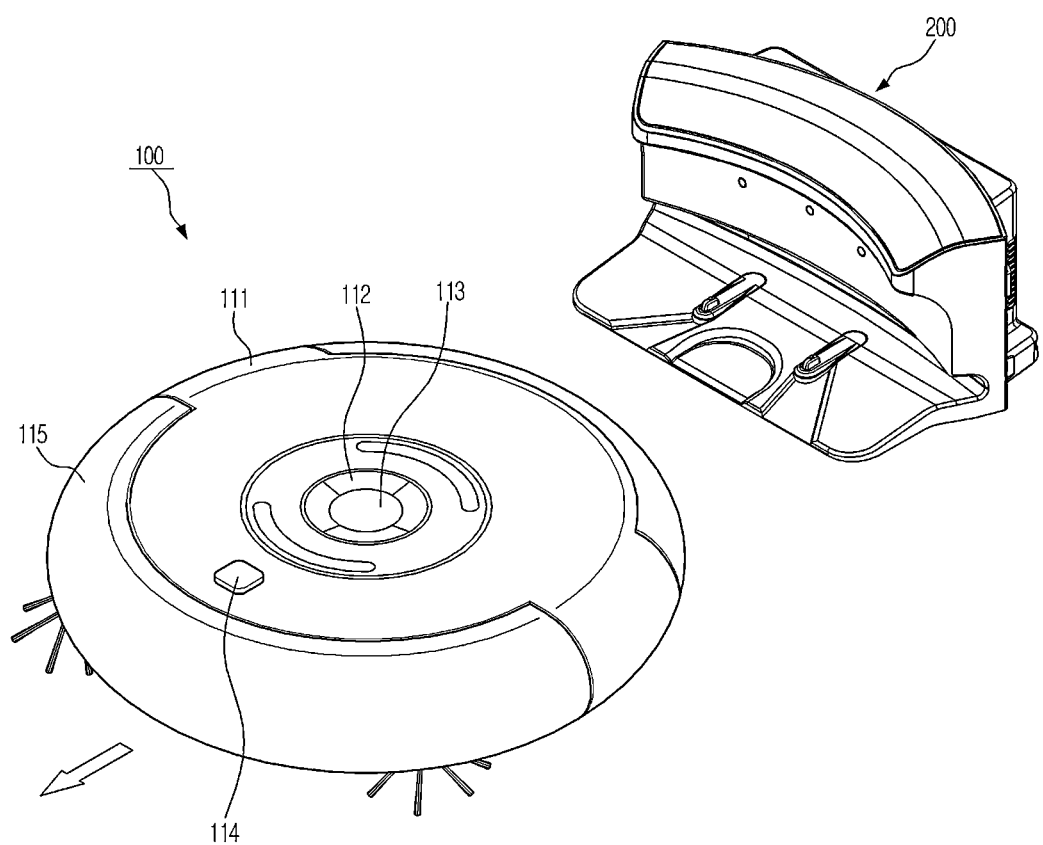
FIGS. 1 and 2 illustrate a robot cleaner according to an embodiment of the present disclosure.

Reference will now be made in detail to embodiments of the present disclosure, examples of which are illustrated in the accompanying drawings, wherein like reference numerals refer to like elements throughout.

Figure 2:
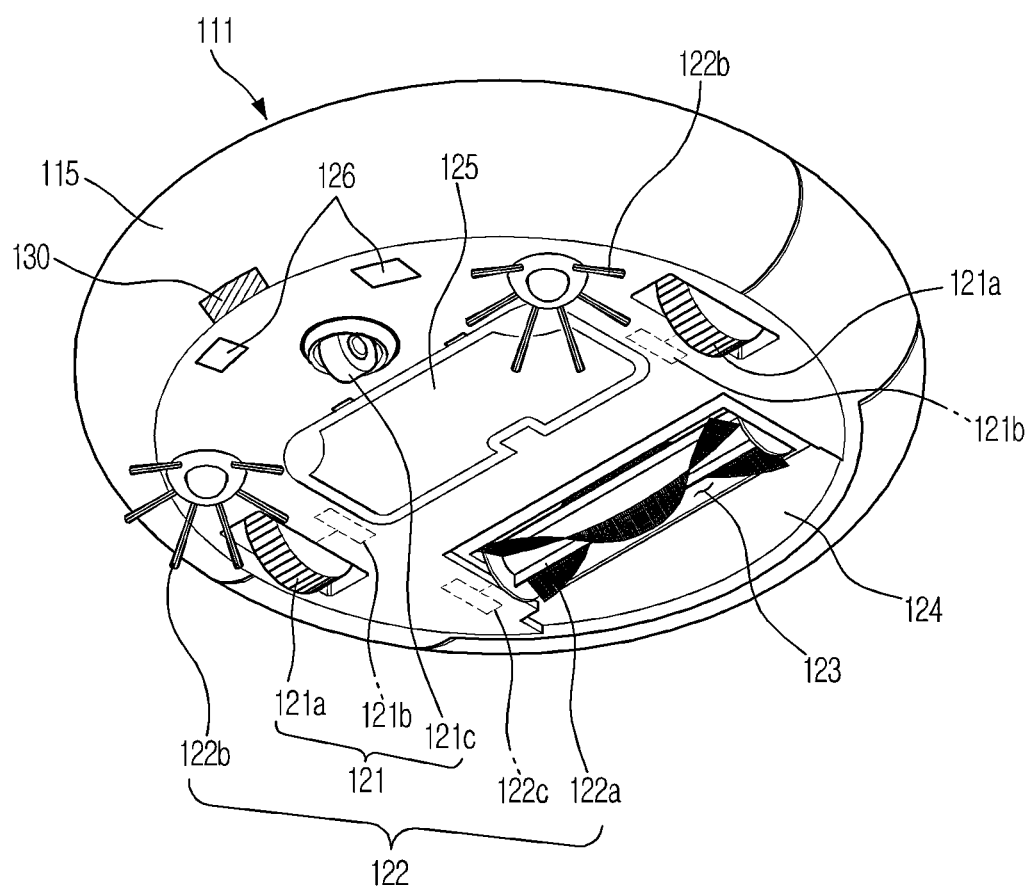

FIGS. 1 and 2 illustrate a robot cleaner 100 according to an embodiment of the present disclosure. In detail, FIG. 1 is a top perspective view of the robot cleaner 100 along with a docking station or recharging base 200, and FIG. 2 is a bottom perspective view of the robot cleaner 100.

When a cleaning command is received from a user or when the system clock reaches a scheduled time, the robot cleaner 100 autonomously travels about an area to be cleaned to suck up foreign substances such as dust present on a floor or to wipe the dust off the floor, thereby cleaning the floor. If cleaning is completed or if a battery voltage drops below a reference voltage, the robot cleaner 100 docks with a recharging base 200. When docking is completed, the robot cleaner 100 receives power from the recharging base 200 and becomes charged.

The docking station or recharging base 200 includes a transformer connected to an external commercial alternating current power supply to receive commercial alternating current power and to convert the received commercial alternating current power, a rectifier for half-wave or full-wave rectifying of the converted power, a smoothing unit for smoothing the rectified power, and a voltage regulator for outputting the smoothed power as direct current power having a predetermined voltage. The direct current power output from the voltage regulator is supplied to the robot cleaner 100 through a power terminal.

During cleaning, the robot cleaner 100 determines a distance to an obstacle, e.g., furniture, office supplies, walls, etc., in a floor to be cleaned, using a distance sensor, acquires and analyzes information about the surface of the floor, and drives the wheels selectively according to the determined distance and the analyzed information about the floor surface to change a traveling direction, thereby cleaning the floor.

The robot cleaner 100 travels along a predetermined pattern or a random pattern based on pre-stored map information to clean the floor.

As illustrated in FIG. 1, the robot cleaner 100 may include, for example, a main body 111 forming an external appearance, an input unit 112 mounted on the main body 111 to receive operation information, schedule information, etc., a display unit 113 mounted on the main body 111 to display operation information, an imaging unit 114 mounted on the main body 111 to acquire an image of a floor to be cleaned during cleaning, and a bumper 115 disposed at the front part of the main body 111 to cushion the impact when the robot cleaner 100 collides with an obstacle.

Additionally, another bumper 115 may be disposed at the back part of the main body 111.

As illustrated in FIG. 2, the robot cleaner 100 may include a traveling unit 121 installed in the lower part of the main body 111 to move the robot cleaner 100, and a brush unit 122 installed in the lower part of the main body 111 to sweep or scatter dust off a floor.

The traveling unit 121 includes a pair of wheels 121a provided in the facing side edges of the main body 111 to move the robot cleaner 100 forward and backward or rotate the robot cleaner 100, first motors 121b which are wheel motors for supplying a driving force to the respective wheels 121a, and a caster wheel 121c installed in the front part of the main body 111 to rotate the robot cleaner 100 according to the surface state of a floor on which the robot cleaner 100 is traveling so that the robot cleaner 100 travels in a different direction.

The caster wheel 121c also acts to support the robot cleaner 100, thereby settling the robot cleaner 100 and preventing the robot cleaner 100 from falling down. The caster wheel 125 is fabricated in the shape of a roller or a caster.

The brush unit 122 includes a main brush 122a provided in an inlet aperture 123 formed in the lower part of the main body 111, and a pair of side brushes 122b provided in the lower part of the front portion of the main body 111 and positioned with the caster wheel 125 disposed in between each of the side brushes 122b.

The main brush 122a functions to sweep dust from a floor, thereby improving the efficiency of the suction of the dust.

The main brush 122a includes a roller and a brush element, and rotates by means of a second motor 122c, which is a brush motor.

The side brushes 122b sweep dust existing below the front part of the robot cleaner 100 and dust located at areas that the main brush 132 cannot cover toward the inlet aperture 123, thereby enhancing the efficiency of cleaning.

The robot cleaner 100 may further include a dust container 124 installed near the main brush 122a to collect foreign substances such as dust gathered through the main brush 122a. The robot cleaner 100 may collect foreign substances such as dust using a suction force.

In addition, the robot cleaner 100 may further include a rag (not shown) for wet cleaning in the inlet aperture 123. The rag may be disposed around the main brush 122a together with the main brush 122a, or independently disposed instead of the main brush 122a.

The robot cleaner 100 includes a battery unit 125 for supplying driving power to driving units including the wheel motors 121b and the brush motor 122c, and recharging terminals 126 electrically connected to the battery unit 125 and to be electrically connected to the recharging base 200 upon docking with the recharging base 200.

The battery unit 125 is a secondary rechargeable battery. The battery unit 150 is electrically connected to the recharging base 200 through the two recharging terminals 126 to receive power from the recharging base 200, thereby being charged.

The robot cleaner 100 further includes at least one ultrasonic sensor 130 for acquiring information about an object located in an area to be cleaned, wherein the object may be a floor surface, and the information about the object may include information about a composition or material of the floor surface, and information about the mechanical properties (roughness, a degree of elasticity, etc.) of the floor surface.

The ultrasonic sensor 130 is positioned such that a part that oscillates an ultrasonic wave faces a floor. This will be described in more detail with reference to FIG. 3, below.

FIG. 3 illustrates examples of installation locations of the ultrasonic sensor 130 included in the robot cleaner 100 according to an embodiment of the present disclosure.

Figure 3A:
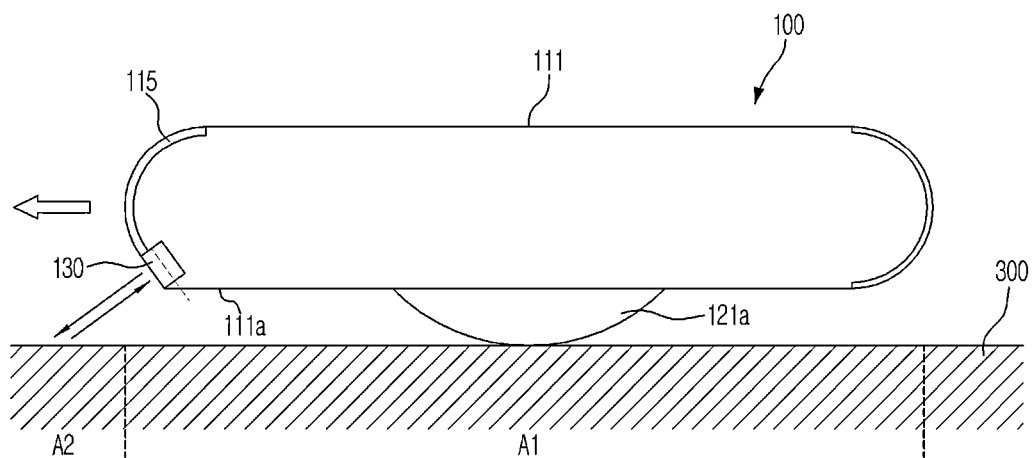
FIGS. 3A and 3B illustrate examples of installation locations of an ultrasonic sensor included in the robot cleaner according to an embodiment of the present disclosure.

Referring to FIG. 3A, the ultrasonic sensor 130 of the robot cleaner 100 is disposed at the lower corner of the front part of the main body 111.

The ultrasonic sensor 130 is installed in a direction diagonal to the main body 111 while making a specific predetermined angle with respect to the lower part 111a of the main body 111. Thereby, a direction in which an ultrasonic wave oscillates is diagonal to a floor surface 300, which is a horizontal plane, and accordingly, an ultrasonic wave from the ultrasonic sensor 130 is emitted toward an area A2 located in front of an area A1 in which the main body 111 of the robot cleaner 100 is currently located.

Thereby, during traveling of the robot cleaner 100, the ultrasonic sensor 130 may detect a floor surface of an area to which the robot cleaner 100 is about to travel, not an area in which the robot cleaner 100 is currently located. That is, the robot cleaner 100 is able to acquire information about a floor surface of an area in which the robot cleaner 100 will next travel, before entering the area, e.g. area A2.

Figure 3B:
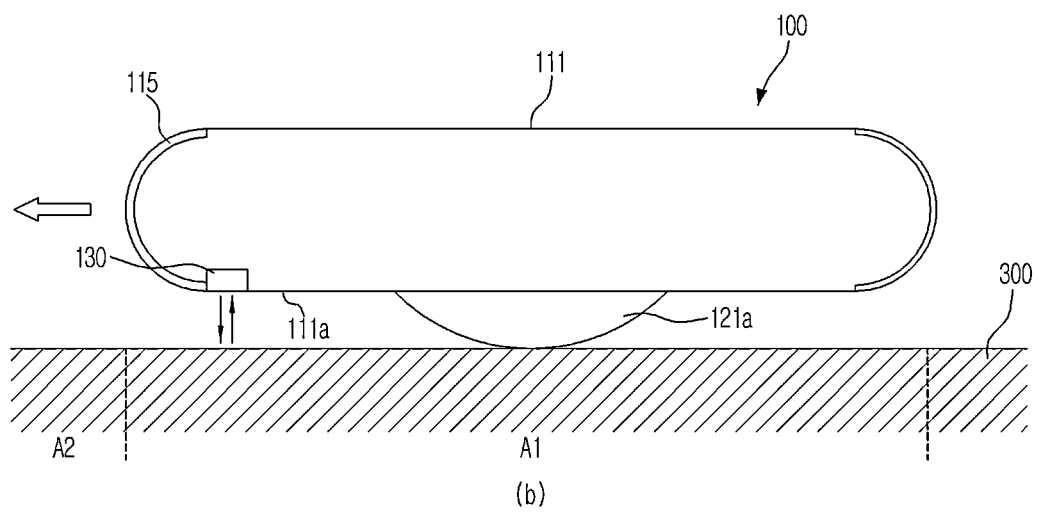

Referring to FIG. 3B, the ultrasonic sensor 130 of the robot cleaner 100 is disposed in the lower part 111a of the main body 111.

In more detail, the ultrasonic sensor 130 is positioned at the front edge of the lower part 111a of the main body 111. In this case, an ultrasonic wave-oscillating part of the ultrasonic sensor 130 is parallel to the lower part 111a of the main body 111, and accordingly, a direction in which an ultrasonic wave from the ultrasonic sensor 130 oscillates is perpendicular to a floor surface that is a horizontal plane.

That is, the robot cleaner 100 may acquire information about a floor surface (that is, the area A1 in which the robot cleaner 100 is currently located) on which the robot cleaner 100 is currently traveling by using the ultrasonic sensor 130 installed in the lower part 111a of the main body 111.

Also, since the ultrasonic sensor 130 is located in front of the wheels 121a, the ultrasonic sensor 130 enables the robot cleaner 100 to determine the existence of an object to be avoided, such as water, a carpet, a hole or an empty space, etc., in advance before encountering the object.

That is, the robot cleaner 100 includes one or more ultrasonic sensors, and acquires information about the floor surface based on ultrasonic waves oscillated from and received by the ultrasonic sensors.

Hereinafter, installation types of the ultrasonic sensor 130 installed in the lower part 111a of the main body 111 of the robot cleaner 100, as illustrated in FIG. 3B, will be described with reference to FIG. 4.

Figure 4A:
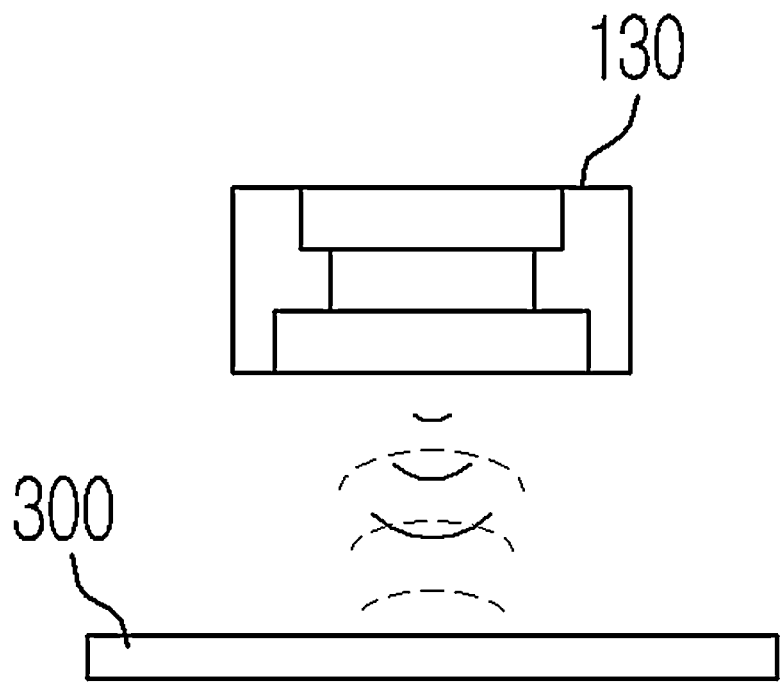
FIGS. 4A and 4B illustrate examples of installation types of the ultrasonic sensor included in the robot cleaner according to an embodiment of the present disclosure.
Figure 4B:
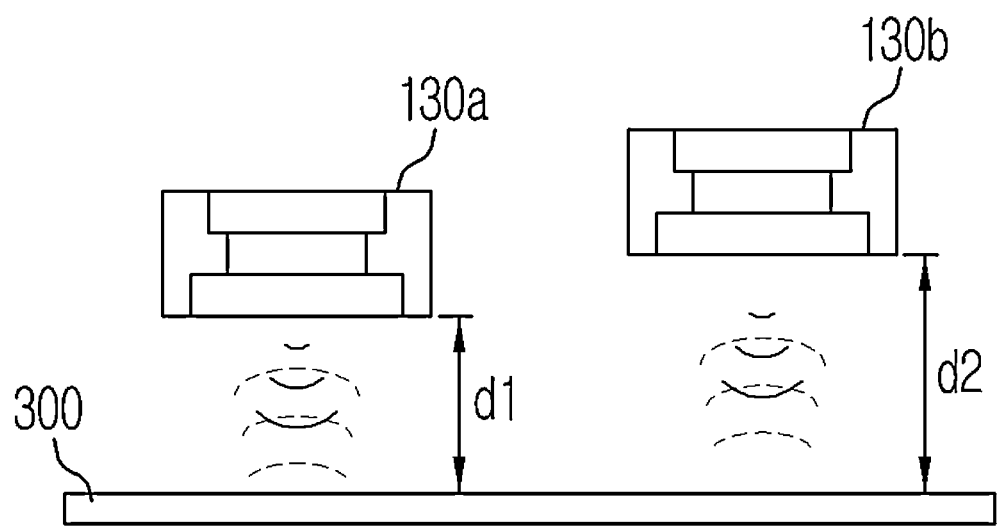

FIG. 4 illustrates examples of installation types of the ultrasonic sensor 130 included in the robot cleaner 100 according to an embodiment of the present disclosure. FIG. 4A shows an example in which a single ultrasonic sensor 130 is installed in the main body 111 of the robot cleaner 100, and FIG. 4B shows an example in which two ultrasonic sensors 130a and 130b (or a plurality of ultrasonic sensors) are installed in the main body 111 of the robot cleaner 100.

Referring to FIG. 4A, the ultrasonic sensor 130 of the robot cleaner 100 is a single ultrasonic sensor.

The ultrasonic sensor 130 performs both functions including oscillating an ultrasonic wave and receiving a reflection wave reflected from a floor surface 300.

A distance between the ultrasonic sensor 130 and the floor surface 300 is a distance at which all or a part of a reflection wave is received while an ultrasonic wave is oscillated from the ultrasonic sensor 130, and at which the ultrasonic wave overlaps the reflection wave.

That is, when the ultrasonic sensor 130 receives a reflection wave while oscillating an oscillation wave, the ultrasonic sensor 130 generates voltage signals in which vibration generated by the oscillation wave and vibration generated by aftershocks received after the oscillation are added to the vibration of the reflection wave. In detail, the ultrasonic sensor 130 successively generates a voltage signal of a composite wave appearing when vibration of the oscillation wave is added with vibration of the reflection wave, and a voltage signal of a composite wave appearing when vibration of aftershock is added with vibration of the reflection wave.

Alternatively, the ultrasonic sensor 130 generates a voltage signal of a composite wave appearing when an aftershock is added with a reflection wave, when the reflection wave is received while the aftershock is generated after an oscillation wave is emitted.

Referring to FIG. 4B, the robot cleaner 100 includes two ultrasonic sensors consisting of first and second ultrasonic sensors 130a and 130b.

Both the first and second ultrasonic sensors 130a and 130b perform both functions including oscillating ultrasonic waves and receiving reflection waves reflected from a floor surface 300.

The second ultrasonic sensor 130b is positioned at a longer distance to the floor surface 300 than the first ultrasonic sensor 130a such that the first and second ultrasonic sensors 130a and 130b have different distances to the floor surface 300.

That is, a distance between the first ultrasonic sensor 130a and the floor surface 300 is d1, a distance between the second ultrasonic sensor 130b and the floor surface 300 is d2, and a difference between d2 and d1 is a distance for causing ultrasonic waves oscillated from the first and second ultrasonic sensors 130a and 130b to have a ¼ wavelength difference.

By using two ultrasonic sensors installed at different distances to a floor surface, it is possible to obtain waveforms generated by different interferences with respect to a floor surface made of the same material. This will be described in detail with reference to FIG. 5, below.

Figure 5:
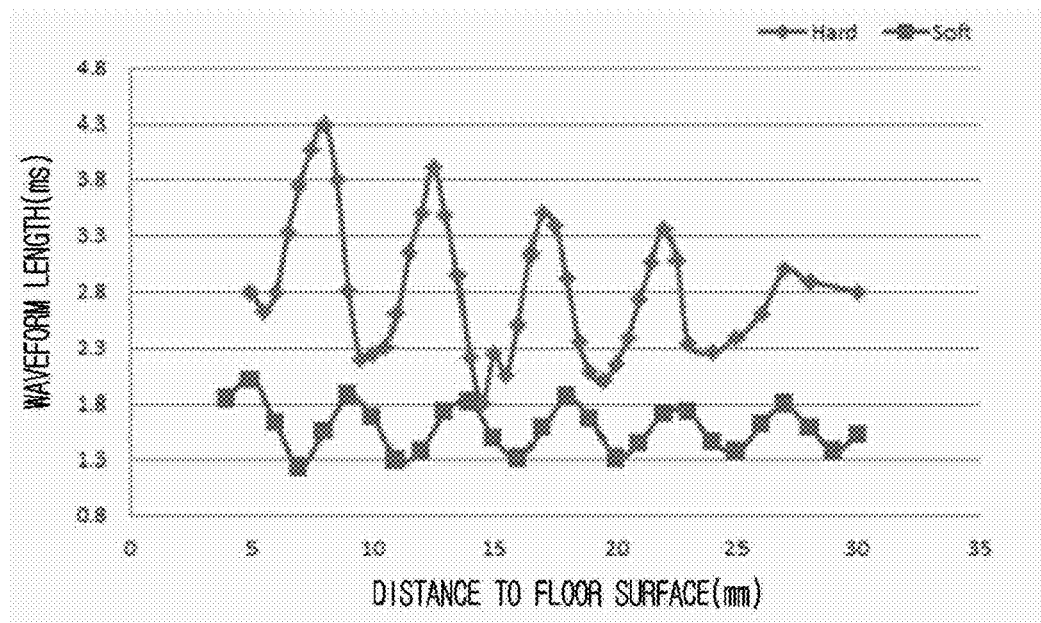
FIG. 5 is a graph showing waveform lengths with respect to distances between a floor and the ultrasonic sensor included in the robot cleaner according to an embodiment of the present disclosure.

FIG. 5 is a graph showing waveform lengths with respect to distances between a floor surface and the ultrasonic sensor 130 included in the robot cleaner 100 according to an embodiment of the present disclosure.

Referring to FIG. 5, a waveform length depends on a distance between the ultrasonic sensor 130 and the floor surface regardless of whether a material of the floor surface is a hard material or a soft material.

A waveform length is the length of a wavelength for a time period for which the amplitude of the waveform is maintained above a predetermined magnitude.

If the ultrasonic sensor 130 operates at a frequency of 40 kHz, since a time period (1 cycle) of 1 wavelength is 25 μm, and velocity of acoustic signals is 340 m/s, a 1 wavelength is 8.5 mm, and a ¼ wavelength is about 2.1 mm.

That is, a waveform length increases or decreases in a unit of a ¼ wavelength.

That a waveform length increases or decreases in a unit of a ¼ wavelength means that destructive interference and constructive interference alternately occur in a composite wave in a unit of a ¼ wavelength. If constructive interference occurs between an oscillation wave and a reflection wave, a waveform length of a composite wave is lengthened, whereas if destructive interference occurs between an oscillation wave and a reflection wave, a waveform length of a composite wave is shortened.

This will be described in more detail, below.

An ultrasonic sensor receives a reflection wave when a piezoelectric device (not shown) vibrates by oscillation or aftershock. At this time, if constructive interference occurs, vibration energy generated by the reflection wave is added to vibration energy generated by oscillation or the aftershock so that total vibration energy increases, and if destructive interference occurs, vibration energy generated by oscillation or the aftershock is cancelled by vibration energy generated by the reflection wave so that total vibration energy decreases.

In other words, when constructive interference occurs, the polarity of a voltage generated by a piezoelectric device (not shown) according to oscillation or aftershock of an ultrasonic sensor is identical to that of a voltage generated by the piezoelectric device according to reception of a reflection wave for each time period so that the magnitude of a total voltage increases, whereas when destructive interference occurs, the polarity of the voltage generated by the piezoelectric device (not shown) according to oscillation or aftershock of the ultrasonic sensor is opposite to that of the voltage generated by the piezoelectric device according to reception of a reflection wave for each time period so that the magnitude of a total voltage decreases.

Also, the ultrasonic sensor outputs a voltage corresponding to the vibration until the vibration disappears. At this time, since vibration energy generated when constructive interference occurs is higher than vibration energy generated when destructive interference occurs, a time period for which the ultrasonic sensor vibrates when constructive interference occurs is longer than a time period for which the ultrasonic sensor vibrates when destructive interference occurs.

Vibration energy of an ultrasonic sensor is reduced over time due to air friction force, etc., and two ultrasonic sensors installed under the same environmental conditions are subject to the same air friction force, etc.

In other words, since vibration energies of two ultrasonic sensors causing different interferences are reduced at constant rates, a time period for which an ultrasonic sensor having higher vibration energy vibrates is longer than a time period for which the remaining ultrasonic sensor vibrates.

That is, since a time period for which a voltage is measured when destructive interference occurs is shorter than a time period for which a voltage is measured when constructive interference occurs, a waveform length appearing when destructive interference occurs is shorter than a waveform length appearing when constructive interference occurs.

As such, since the first and second ultrasonic sensors 130a and 130b have a distance difference of a ¼ wavelength, it is possible to detect waveforms generated by different interferences with respect to a floor surface made of the same material.

Also, it is possible to acquire waveforms generated by different interferences according to a material of a floor surface when an ultrasonic sensor is located at the same distance to the floor surface. The reason is because reflection at a free end or reflection at a fixed end occurs according to whether a material of a floor surface is a soft material or a hard material.

For example, when a distance between an ultrasonic sensor and a floor surface is 9 mm, a waveform length was calculated as 2.2 ms in the case in which the floor surface is made of a hard material. The waveform length is shorter than those calculated at distances of 8 mm and 10 mm, and accordingly, it can be expected that destructive interference has occurred. Meanwhile, when the floor surface is made of a soft material, a waveform length was calculated as 1.9 ms, and the waveform length is longer than those calculated at distances of 8 mm and 10 mm. Accordingly, it can be expected that constructive interference has occurred.

As such, the robot cleaner 100 may determine a material of a floor surface through analysis of interference waveforms according to materials of a floor surface, and also may improve accuracy of a determination of the material of the floor surface through analysis of interference waveforms detected by a plurality of ultrasonic sensors having different distances to the floor surface.

In addition, a plurality of ultrasonic sensors may be disposed with a curved arrangement in the main body 111 of the robot cleaner 100 in order to widen a sensing range.

Figure 6:
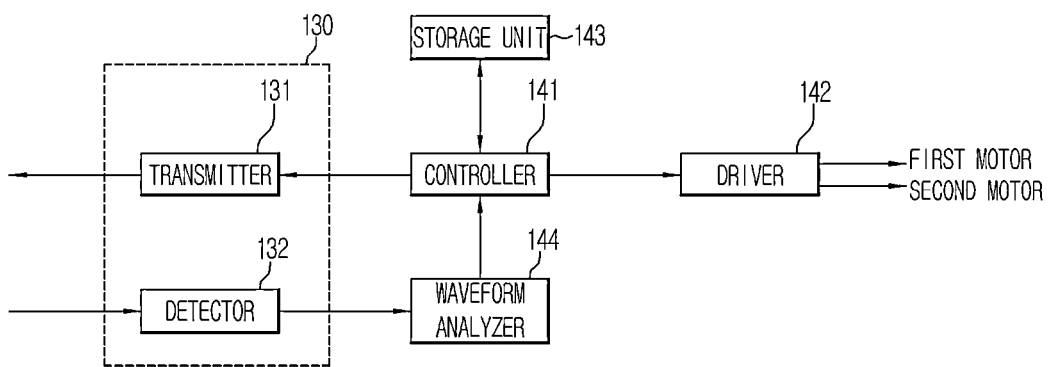
FIG. 6 is a block diagram illustrating the robot cleaner according to an embodiment of the present disclosure.

FIG. 6 is a block diagram illustrating the robot cleaner according to an embodiment of the present disclosure. Referring to FIG. 6, the robot cleaner 100 may include an ultrasonic sensor 130, a controller 141, a driver 142, a storage unit 143, and a waveform analyzer 144.

The ultrasonic sensor 130 generates ultrasonic waves, receives reflection waves from the outside, and detects and outputs a voltage which is an electrical signal that varies according to vibration of oscillation waves and vibration of reflection waves. The ultrasonic sensor 130 includes a transmitter 131 and a detector 132.

The transmitter 131 changes voltage values that are applied to both electrodes (not shown) of the ultrasonic sensor 130 according to a command from the controller 141 so that the ultrasonic sensor 130 emits ultrasonic waves toward a floor surface.

In order for the ultrasonic sensor 130 to oscillate at an oscillation frequency according to the command from the controller 141, the transmitter 131 amplifies a voltage supplied from a power supply (not shown) to a voltage corresponding to the oscillation frequency.

The detector 132 detects a voltage, which is an electrical signal generated in the ultrasonic sensor 130, and outputs the voltage to the wave analyzer 144.

Voltage signals detected by the detector 132 are voltage signals that are output from the ultrasonic sensor 130 when an ultrasonic wave oscillates or is received. The voltage signals include a voltage signal according to a vibration of an oscillation wave, a voltage signal according to a vibration of a reflection wave, and a voltage signal of a composite wave appearing when the vibration of the oscillation wave overlaps the vibration of the reflection wave.

The voltage signals that are output from the ultrasonic sensor 130 further include a voltage signal of a composite wave appearing when vibration of an aftershock generated after oscillation of the ultrasonic wave overlaps the vibration of the reflection wave.

That is, voltages corresponding to vibrations of an oscillation wave, a composite wave, and a reflection wave are generated over time. At this time, a voltage which is an electrical signal output from the ultrasonic sensor 130 is a detection wave.

That is, the detector 132 outputs a detection wave having a voltage value varying over time to the waveform analyzer 144.

If a cleaning command or a traveling command is received through the input unit (112 of FIG. 1), the controller 141 controls at least one of a cleaning mode and a traveling mode based on pre-stored map information. In detail, the controller 141 controls driving of the transmitter 131 and the detector 132, compares a waveform length of a detection wave transmitted from the waveform analyzer 144 to a first reference waveform length to determine information about a floor surface, and controls at least one of a cleaning mode and a traveling mode based on the determined information about the floor surface.

Here, the waveform length is a time period spanning from a time at which the detection wave has been detected to a time at which a voltage of the detection wave has reached 0V.

Also, the waveform length may be decided as a time period at which the amplitude of a detection wave detected by the detector 144 is maintained above a predetermined magnitude.

The controller 141 determines whether to perform avoidance traveling or continuous traveling based on the determined information about the floor surface, controls driving of the first motors (121b of FIG. 2) according to the result of the determination to change a traveling direction and a traveling speed, and also controls a driving of the second motor (122c of FIG. 2) to change a cleaning mode.

Here, the cleaning mode includes a hard mode and a soft mode which are classified according to a material of a floor surface. If a cleaning mode changes, a sucking force and a rotation speed of the main brush (122a of FIG. 2) change accordingly.

Also, the cleaning mode may further include a wet mode and a dry mode.

The driver 142 drives the first motors 121b according to a command from the controller 141 to change a travelling speed and a traveling direction, and also drives the second motor 122c according to a command from the controller 141 to change a rotation speed of the main brush 122a or stop a rotation of the main brush 122a.

The storage unit 143 stores a first reference waveform length for distinguishing a hard material from a soft material.

The waveform analyzer 144 calculates a generation time period of a waveform from a time at which a detection wave has been received to a time at which a voltage of the waveform of the detection wave attenuates to 0V, decides the generation time period of the waveform as a waveform length, and then transmits the waveform length to the controller 141.

Also, the waveform analyzer 144 may calculate a maintenance time period for which the amplitude of the detection wave is maintained above a predetermined magnitude, decide the maintenance time period as a waveform length, and transmit the waveform length to the controller 141.

Figure 7:
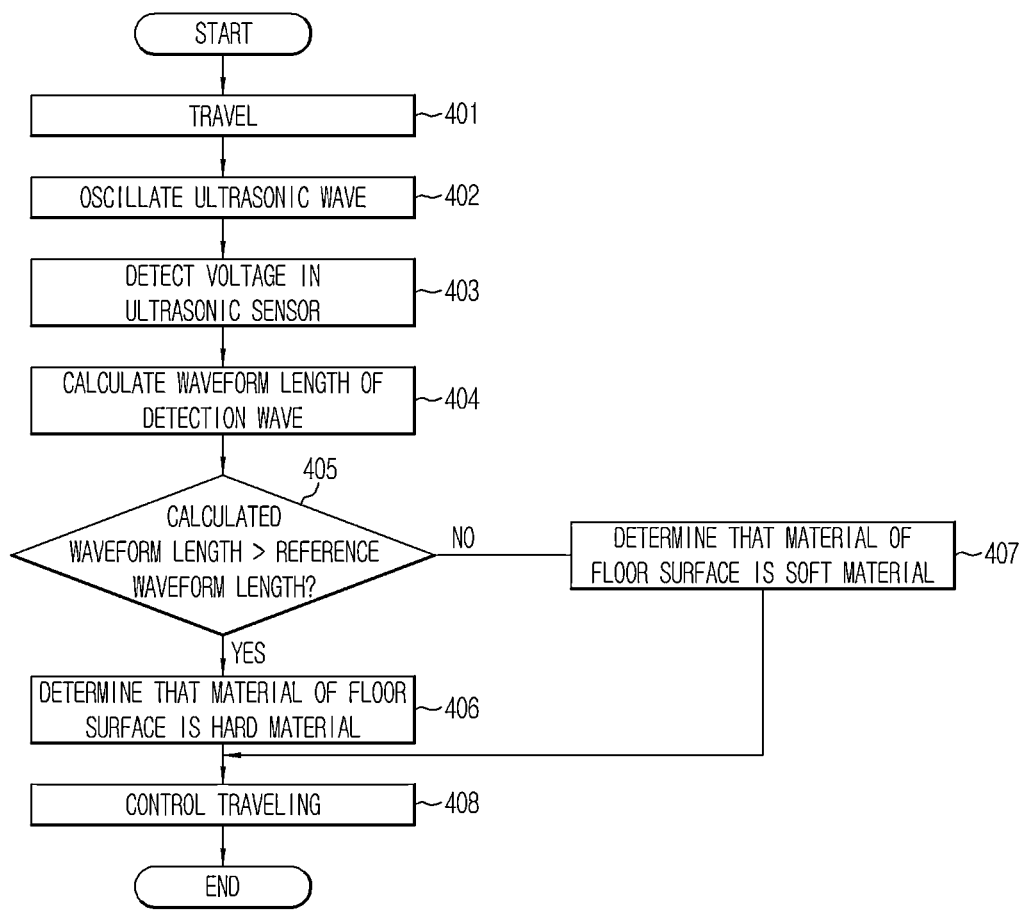
FIG. 7 is a flowchart illustrating a method of controlling the robot cleaner according to an embodiment of the present disclosure.

FIG. 7 is a flowchart illustrating a method of controlling the robot cleaner 100 according to an embodiment of the present disclosure. The control method of the robot cleaner 100 will be described with reference to FIGS. 8 and 9, below.

Referring to FIGS. 1, 2 and 7, if a cleaning command or a traveling command is received through the input unit 112, the robot cleaner 100 drives the first motors 121b and the second motor 122c based on pre-stored map information.

That is, the robot cleaner 100 drives the first motors 121b to rotate the wheels 121a, thereby travelling (401), and also, the robot cleaner 100 drives the second motor 122c to rotate the main brush 122a, thereby performing cleaning.

During traveling and cleaning, the robot cleaner 100 drives the ultrasonic sensor 130 to oscillate an ultrasonic wave toward a floor surface (402). Then, the ultrasonic sensor 130 receives a reflection wave from an external object.

Figure 8:
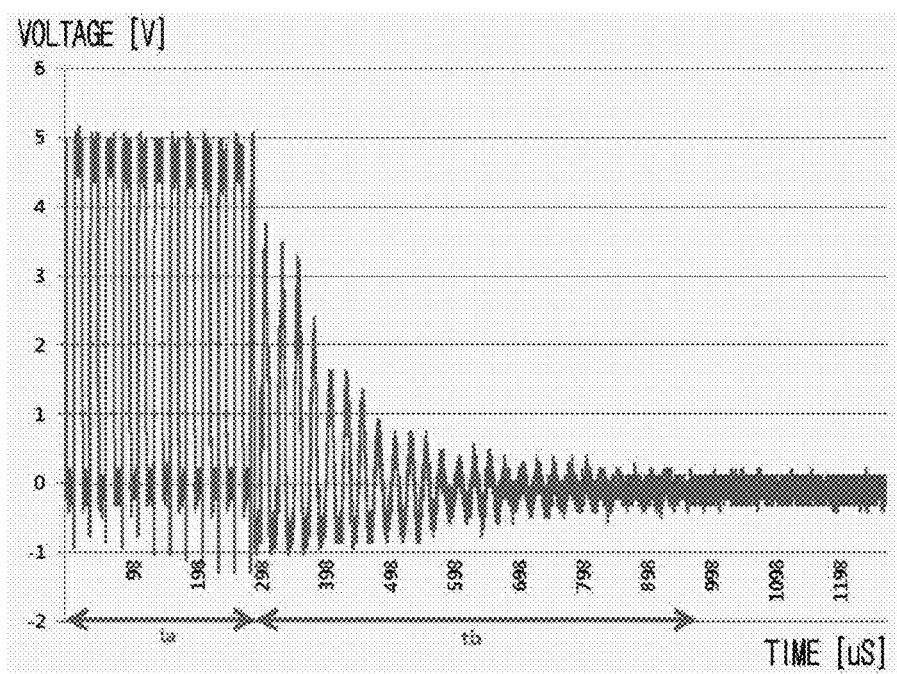
FIG. 8 is a graph showing a voltage output from the ultrasonic sensor of the robot cleaner according to an embodiment of the present disclosure after the ultrasonic sensor has oscillated an ultrasonic wave.

Referring to FIG. 8, the transmitter of an ultrasonic sensor applies an alternating current voltage of about 5V to electrodes of the ultrasonic sensor for a predetermined time period $t_a$ so that a piezoelectric device oscillates. At this time, the piezoelectric device is compressed and extends according to an amplitude and a frequency period corresponding to the alternating current voltage of 5V, and vibrates by the compression and extension. The detector of the ultrasonic sensor detects a voltage of a frequency corresponding to the alternating current voltage of 5V for the predetermined time period $t_a$.

If the voltage of 5V is no longer applied to the electrodes of the ultrasonic sensor after the predetermined time period $t_a$ elapses, the piezoelectric device of the ultrasonic sensor is subject to an aftershock for a predetermined time period $t_b$ by inertia for the vibration generated for the predetermined time period $t_a$, and the detector of the ultrasonic sensor detects a voltage corresponding to the aftershock for the predetermined time period tb.

The intensity of the aftershock is gradually reduced over time by air resistance, air friction force, etc., and accordingly, the magnitude of the corresponding voltage is also reduced over time.

A time at which a reflection wave is received depends on a distance between the ultrasonic sensor and the floor surface, and corresponds to a time at which an oscillation wave is generated or a time at which an aftershock is generated.

That is, if a reflection wave is received at a time at which an oscillation wave is generated, the ultrasonic sensor outputs a composite wave appearing when the oscillating wave overlaps the reflection wave and the aftershock overlaps the reflection wave. If a reflection wave is received at a time at which the aftershock is generated, the ultrasonic sensor outputs a composite wave appearing when vibration by the aftershock overlaps vibration by the reflection wave.

While ultrasonic waves oscillate and are received, the robot cleaner 100 detects a voltage signal according to the oscillation and reception of the ultrasonic waves (403), amplifies the detected voltage signal to a predetermined magnitude, and then performs filtering for blocking noise corresponding to a low frequency band and passing only a high frequency band.

Then, the robot cleaner 100 acquires and analyzes a detection wave, which is a voltage waveform appearing for the detection time period. The detection wave includes an oscillation wave, a reflection wave, a composite wave appearing when destructive interference or constructive interference has occurred after the oscillation wave has overlapped the reflection wave, and a composite wave appearing when destructive interference or constructive interference has occurred after an aftershock has overlapped the reflection wave.

Then, the robot cleaner 100 calculates a generation time period of the waveform, which occurs from a time at which the detection wave has been detected to a time at which a voltage of the waveform of the detection wave attenuates to 0V, and calculates a waveform length corresponding to the generation time period of the waveform (404).

Also, the robot cleaner 100 may calculate a maintenance time period for which the waveform is maintained with a constant amplitude in the generation time period, from the time at which the detection wave has been detected to the time at which the waveform of the detection wave starts to attenuate, and may calculate a waveform length corresponding to the maintenance time period.

At this time, the generation time period of the composite wave depends on whether constructive interference or destructive interference has occurred between the reflection wave and the aftershock.

That is, if constructive interference has occurred, a time period for which the piezoelectric device vibrates is relatively long since vibration energy for vibrating the piezoelectric device is high, whereas if destructive interference has occurred, a time period for which the piezoelectric device vibrates is relatively short since vibration energy for vibrating the piezoelectric device is low.

This will be described in detail with reference to FIG. 9, below.

Figure 9:
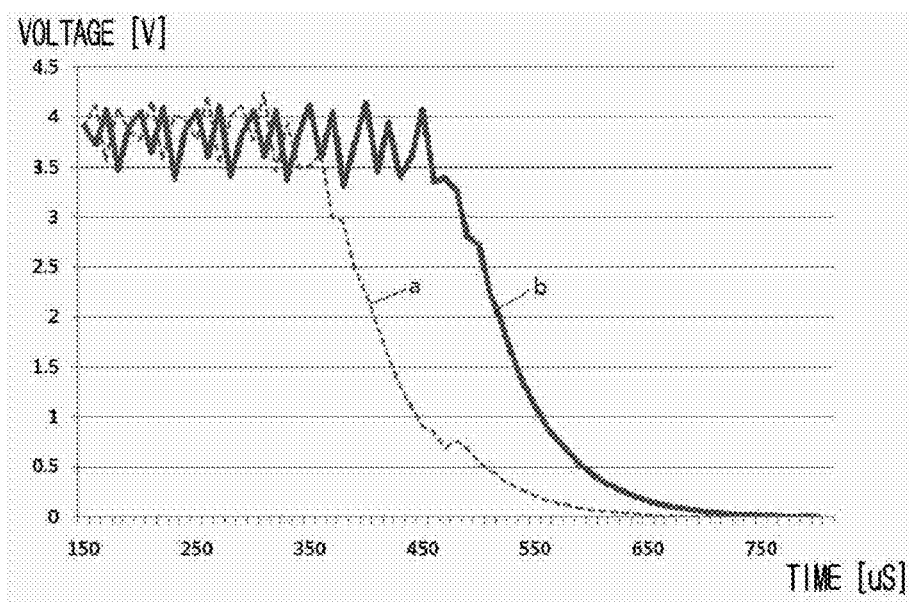
FIG. 9 is a graph showing voltages with respect to floor materials, output from the ultrasonic sensor of the robot cleaner according to an embodiment of the present disclosure.

A graph a of FIG. 9 is a graph showing a waveform of a detection wave with respect to a floor surface made of a soft material, and a graph b of FIG. 9 is a graph showing a waveform of a detection wave with respect to a floor surface made of a hard material. The graphs a and b of FIG. 9 corresponds to an example in which destructive interference occurs when a reflection wave reflected from a floor surface made of a soft material is received, and constructive interference occurs when a reflection reflected from a floor surface made of a hard material is received.

Waveform lengths according to generation times of the waveforms were calculated, as follows.

As seen in the graph a of FIG. 9, a waveform length of a detection wave with respect to a floor surface made of a soft material is about 640 μm, and as seen in the graph b of FIG. 9, a waveform length of a detection wave with respect to a floor surface made of a hard material is about 710 μm. That is, a waveform length of a detection wave generated by receiving a reflection wave reflected from a floor surface made of a soft material is different from that of a detection wave generated by receiving a reflection wave reflected from a floor surface made of a hard material.

Meanwhile, waveform lengths according to maintenance time periods of the waveforms are obtained as follows.

As seen in the graph a of FIG. 9, a waveform length corresponding to a maintenance time period for which a detection wave with respect to a floor surface made of a soft material is maintained with a constant amplitude is about 350 μm, and as seen in the graph b of FIG. 9, a waveform length corresponding to a maintenance time period for which a detection wave with respect to a floor surface made of a hard material is maintained with a constant amplitude is about 450 µm. That is, a waveform length of a detection wave generated by receiving a reflection wave reflected from a floor surface made of a soft material is different from that of a detection wave generated by receiving a reflection wave reflected from a floor surface made of a hard material.

Then, the robot cleaner 100 compares the waveform length to a pre-stored first reference waveform length (405). If the waveform length is longer than the first reference waveform length, the robot cleaner 100 determines that a material of the floor surface is a hard material (406), and if the waveform length is shorter than or equal to the first reference waveform length, the robot cleaner 100 determines that a material of the floor surface is a soft material (407).

The first reference waveform length is a length for determining whether a material of a floor surface is a soft material or a hard material. Referring to FIG. 8, if a waveform length is calculated based on a generation time period of a waveform, the first reference waveform length may be set to about 670 µm, and if a waveform length is calculated based on a maintenance time period of a waveform, the first reference waveform length may be set to about 400 µm.

Then, the robot cleaner 100 controls driving of the first motors according to the result of the determination, thereby controlling a traveling mode (408). Also, the robot cleaner 100 may control the first motors (121b of FIG. 2) and the second motor (122c of FIG. 2) based on the result of the determination, thereby changing a cleaning mode.

An example in which the robot cleaner 100 controls a traveling mode is as follows.

If the robot cleaner 100 determines that the floor surface is made of a soft material, the robot cleaner 100 changes RPMs of the first motors 121b to change a traveling direction, thereby performing avoidance traveling. Meanwhile, if the robot cleaner 100 determines that the floor surface is made of a hard material, the robot cleaner 100 performs continuous traveling based on map information.

Then, an example in which the robot cleaner 100 changes a cleaning mode is as follows.

If the robot cleaner 100 determines that the floor surface is made of a soft material, the robot cleaner 100 determines that a carpet is laid on the floor, and sets a cleaning mode to a carpet mode.

Figure 10:
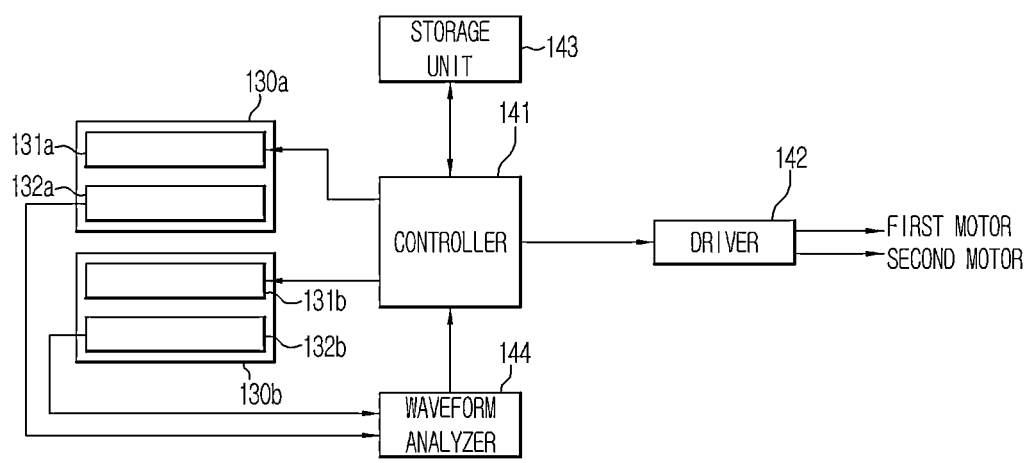
FIG. 10 is a block diagram illustrating a robot cleaner according to another embodiment of the present disclosure.

FIG. 10 is a block diagram illustrating a robot cleaner according to another embodiment of the present disclosure. Referring to FIG. 10, the robot cleaner includes ultrasonic sensors 130a and 130b, a controller 141, a driver 142, a storage unit 143, and a waveform analyzer 144.

The first ultrasonic sensor 130a generates an ultrasonic wave, receives a reflection wave from the outside, and outputs a detection wave according to oscillation and reception. The first ultrasonic sensor 130a includes a transmitter 131a and a detector 132a. Likewise, the second ultrasonic sensor 130b generates an ultrasonic wave, receives a reflective wave from the outside, and outputs a detection wave according to oscillation and reception. The ultrasonic sensor 130b also includes a transmitter 131b and a detector 132b.

The first and second ultrasonic sensors 130a and 130b have different distances to a floor surface.

The detector 132a of the first ultrasonic sensor 130a detects a voltage generated in the first ultrasonic sensor 130 and outputs the detected voltage to the waveform analyzer 144, and the detector 132b of the second ultrasonic sensor 130b detects a voltage generated in the second ultrasonic sensor 130b and outputs the detected voltage to the waveform analyzer 144.

The voltage detected by the detector 132a of the first ultrasonic sensor 130a is a voltage generated in the first ultrasonic sensor 130a when the first ultrasonic sensor 130a oscillates and receives ultrasonic waves, and includes a voltage generated by vibration of an oscillation wave from the first ultrasonic sensor 130a, a voltage generated by vibration of a reflection wave, and a voltage corresponding to a composite wave appearing when the vibration of the oscillation wave overlaps the vibration of the reflection wave.

Also, the voltage detected by the detector 132b of the second ultrasonic sensor 130b is a voltage generated in the second ultrasonic sensor 130b when the second ultrasonic sensor 130b oscillates and receives ultrasonic waves, and includes a voltage generated by vibration of an oscillation wave from the second ultrasonic sensor 130b, a voltage generated by vibration of a reflection wave, and a voltage corresponding to a composite wave appearing when the vibration of the oscillation wave overlaps the vibration of the reflection wave.

The composite wave includes a composite wave appearing when vibration of aftershock overlaps vibration of a reflection wave after the first or second ultrasonic sensor 130a or 130b oscillates an ultrasonic wave.

The voltages output from the first and second ultrasonic sensors 130a and 130b appear over time. The voltages will be hereinafter referred to as first and second detection waves.

The controller 141 controls driving of the first and second ultrasonic sensors 130a and 130b, selects a longer one of waveform lengths of the first and second detection waves transmitted from the waveform analyzer 144, compares the selected waveform length to a second reference waveform length to determine information about a floor surface, and then controls at least one of a cleaning mode and traveling based on the determined information about the floor surface.

Also, the controller 141 may calculate a difference in a waveform length between the first detection wave and the second detection wave, and compares the calculated waveform length difference to a reference value, thereby determining information about a floor surface.

Also, the controller 141 may compare the waveform length of the first detection wave to the waveform length of the second detection wave to determine which one is longer, and determines information about a floor surface based on the result of the determination.

The waveform length may be a generation time period of the waveform from a time at which the corresponding detection wave has been generated to a time at which the amplitude of the detection wave reaches zero, or the waveform length may be a maintenance time period of the waveform for which the amplitude of the corresponding detection wave is maintained above a predetermined magnitude.

The controller 141 determines whether to perform avoidance traveling or continuous traveling based on the determined information about the floor surface, controls driving of the first motors (121b of FIG. 2) based on the result of the determination to change a traveling direction and a traveling speed, and controls driving of the second motor (122c of FIG. 2) to change a cleaning mode.

The driver 142 is the same as the driver 142 of FIG. 6, and accordingly, a detailed description thereof will be omitted.

The storage unit 143 stores the second reference waveform length for distinguishing a hard material from a soft material.

The storage unit 143 may store a reference value for a waveform length difference between first and second detection waves, for distinguishing a hard material from a soft material, and also store information about detection waves with longer waveform lengths with respect to materials of a floor surface.

The waveform analyzer 144 calculates a first maintenance time period from a time at which the first detection wave has been received to a time at which the waveform of the first detection wave starts to attenuate, decides the first maintenance time period as a first waveform length, then transmits the first waveform length to the controller 141, calculates a second maintenance time period from a time at which the second detection wave has been received to a time at which the waveform of the second detection wave starts to attenuate, decides the second maintenance time period to a second waveform length, and then transmits the second waveform length to the controller 141.

Figure 11:
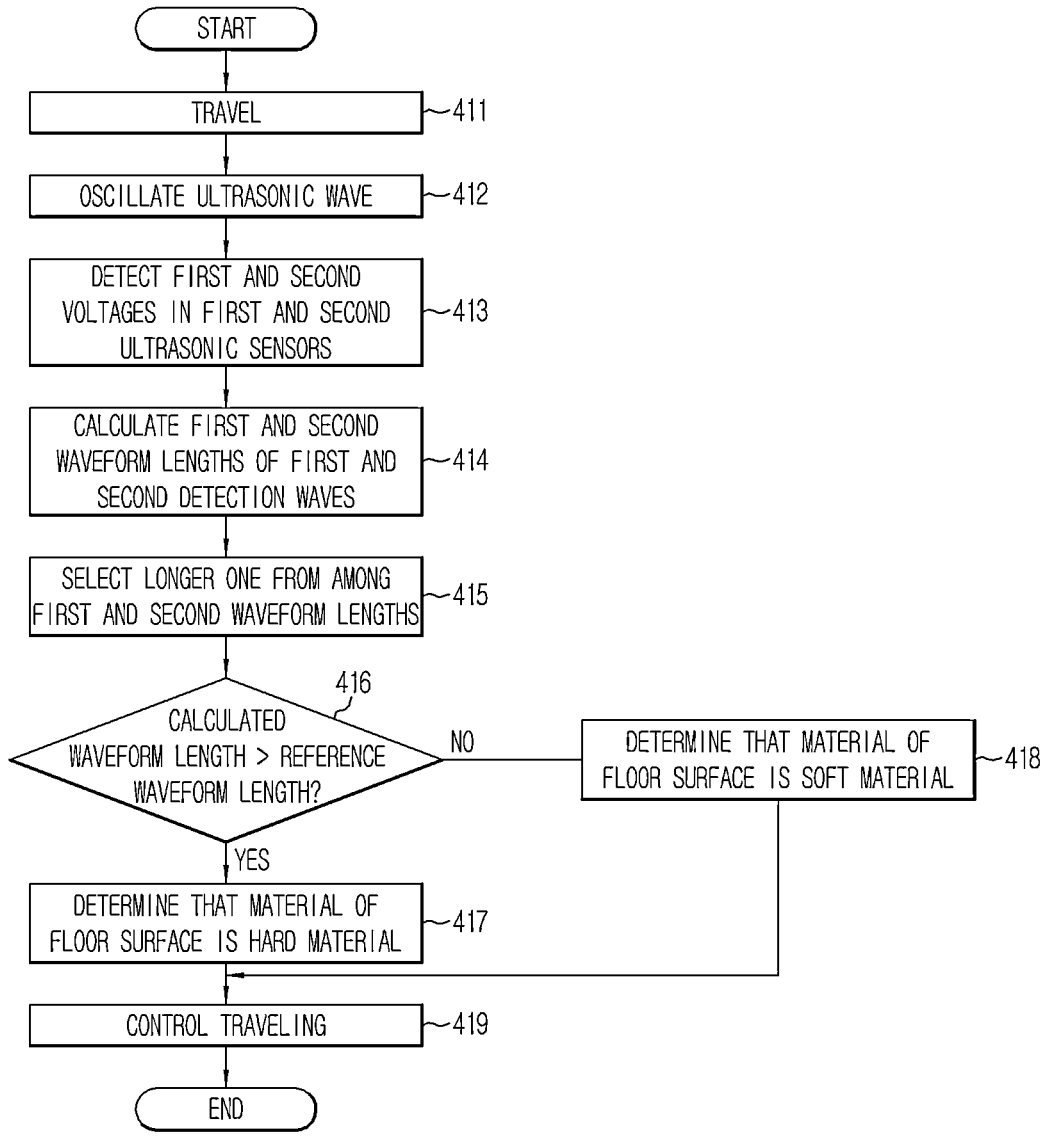
FIG. 11 is a flowchart illustrating a method of controlling the robot cleaner according to another embodiment of the present disclosure.

FIG. 11 is a flowchart illustrating a method of controlling the robot cleaner according to another embodiment of the present disclosure.

Referring to FIGS. 1, 2, 10, and 11, if a cleaning command or a traveling command is received through the input unit 112, the robot cleaner drives the first motors 121*b* to rotate the wheels 121*a*, thereby causing the robot cleaner to travel (411), and drives the second motor 122*c* to rotate the main brush 122*a*, thereby causing the robot cleaner to clean.

During traveling and cleaning, the robot cleaner drives the first and second ultrasonic sensors 130*a* and 130*b* so that the first and second ultrasonic sensors 130*a* and 130*b* emit ultrasonic waves toward a floor surface (412). Thereafter, the ultrasonic waves are received by the first and second ultrasonic sensors 130*a* and 130*b*, respectively.

While the ultrasonic waves are oscillated and received by the first and second ultrasonic sensors 130*a* and 130*b*, the robot cleaner detects voltage signals according to the oscillation and reception of the ultrasonic waves by the first and second ultrasonic sensors 130*a* and 130*b* (413), amplifies the detected voltage signals to predetermined magnitudes, and then performs filtering for blocking noise corresponding to a low frequency band and passing only a high frequency band.

Then, the robot cleaner acquires and analyzes a first detection wave and a second detection wave that represent voltages according to detection times. The first and second detection waves include oscillation waves generated by the first and second ultrasonic sensors 130*a* and 130*b*, reflection waves, and composite waves appearing when destructive interference or constructive interference has occurred after the oscillation waves have overlapped the reflection waves.

Successively, the robot cleaner calculates a first generation time period of the first detection wave from a time at which the first detection wave has been detected to a time at which a voltage of the waveform of the first detection wave reaches 0V, calculates a first waveform length corresponding to the first generation time period, calculates a second generation time period of the second detection wave from a time at which the second detection wave has been detected to a time at which a voltage of the waveform of the second detection wave reaches 0V, and calculates a second waveform length corresponding to the second generation time period (414).

Then, the robot cleaner compares the first waveform length to the second waveform length to select a longer one from among the first and second waveform lengths (415), and compares the selected waveform length to the second reference waveform length (416).

If the selected waveform length is longer than the second reference waveform length, the robot cleaner determines that a material of a floor surface is a hard material (417), whereas if the selected waveform length is shorter than or equal to the second reference waveform length, the robot cleaner determines that a material of the floor surface is a soft material (418).

The second reference waveform length is a length for determining whether a material of a floor surface is a hard material or a soft material.

This will be described in more detail with reference to FIG. 5, below.

It is assumed that the first ultrasonic sensor 130*a* is located a distance of 9 mm from a floor surface and the second ultrasonic sensor 130*b* is located a distance of 13 mm from the floor surface.

In this case, if a waveform length of a first detection wave detected by the first ultrasonic sensor 130*a* is 2.2 ms, and a waveform length of a second detection wave detected by the second ultrasonic sensor 130*b* is 4.0 ms, the robot cleaner compares the waveform length of the first detection wave to the waveform length of the second detection wave, selects the waveform length of the second detection wave, then compares the waveform length of the second detection wave to a second reference waveform length, and determine that a material of the floor surface is a hard material if the waveform length of the second detection wave is longer than the second reference waveform length.

Also, the robot cleaner may calculate first and second waveform lengths based on a maintenance time period for which the amplitude of the corresponding detection wave is maintained with a constant magnitude, the maintenance time period corresponding to a time period from a time at which the detection wave has been detected to a time at which the waveform of the detection wave starts to attenuate.

As another example, the robot cleaner may calculate a difference in a waveform length between the first detection wave and the second detection wave, compare the calculated waveform length difference to a reference value, and determine information about a floor surface based on the result of the comparison.

The example will be described below. In the following description, it is assumed that the first ultrasonic sensor 130*a* is located a distance of 9 mm from a floor surface and the second ultrasonic sensor 130*b* is located a distance of 13 mm from the floor surface.

In this case, the robot cleaner calculates a difference between the waveform length 2.2 ms of the first detection wave and the waveform length 4.0 ms of the second detection wave, and compares the calculated difference 1.8 ms to a reference value to determine a material of the floor surface. If the calculated difference 1.8 ms is greater than the reference value, the robot cleaner determines that a material of the floor surface is a hard material.

Referring to FIG. 5, when a difference in a waveform length is determined in a unit of a ¼ wavelength, a waveform length difference of about 0.5 ms appears if the material of the floor surface is a soft material, and a waveform length difference of about 1.5 ms appears if the material of the floor surface is a hard material. Considering the graph of FIG. 5, the reference value for distinguishing a soft material from a hard material may be set to about 1 ms.

As another example, the robot cleaner may compare the waveform length of the first detection wave to the waveform length of the second detection wave to determine which one is longer, and may determine information about a floor surface based on the result of the determination.

The example will be described below. In the following description, it is assumed that the first ultrasonic sensor 130*a* is located a distance of 9 mm from a floor surface and the second ultrasonic sensor 130b is located a distance of 13 mm from the floor surface.

In this case, the robot cleaner compares a waveform length of a first detection wave to a waveform length of a second detection wave, determines, if the waveform length of the first detection wave is shorter than the waveform length of the second detection wave, that a material of the floor surface is a hard material, and determines, if the waveform length of the first detection wave is longer than the waveform length of the second detection wave, that the material of the floor surface is a soft material.

Then, the robot cleaner controls driving of the first motors 121b based on the result of the determination to thereby control traveling (419). Also, the robot cleaner controls the first and second motors 121b and 122c based on the result of the determination to thereby change a cleaning mode.

Hereinafter, a configuration for controlling the robot cleaner will be described with reference to FIG. 10.

As described above, the robot cleaner includes the plurality of ultrasonic sensors 130a and 130b each having a transmitter (not shown) and a detector (not shown), the controller 141, the storage unit 143, the driver 142, and the waveform analyzer 144.

Since the ultrasonic sensors 130a and 130b and the driver 142 have been described above with reference to FIG. 10, detailed descriptions thereof will be omitted.

The controller 141 controls driving of the transmitter and the detector while performing at least one of a cleaning mode and traveling, determines information about a floor surface based on a result of waveform analysis transferred from the waveform analyzer 144, and controls at least one of the cleaning mode and traveling based on the determined information about the floor surface.

The results of waveform analysis are obtained by determining types of interference waveforms of composite waves in first and second detection waves.

If the controller 141 receives types of interference waveforms of first and second detection waves from the waveform analyzer 144, the controller 141 compares the types of interference waveforms to a plurality of types of reference interference waveforms to determine information about a floor surface.

The plurality of types of reference interference waveforms are types of reference interference waveforms according to materials of a floor surface, and in order to determine information about a floor surface, the controller 141 extracts types of reference interference waveforms corresponding to the first and second ultrasonic sensors 130a and 130b according to materials of a floor surface, and compares the types of interference waveforms to the extracted types of reference interference waveforms.

The storage unit 143 stores the types of reference interference waveforms corresponding to the first and second ultrasonic sensors 130a and 130b according to materials of a floor surface.

The waveform analyzer 144 determines whether types of interference waveforms of the composite waves in the first and second detection waves are a constructive interference waveform or a destructive interference waveform, and transmits the results of the determination to the controller 141. The destructive interference and constructive interference have the properties of reflection at fixed end and reflection at free end.

This will be described in more detail with reference to FIG. 5, below.

It is assumed that the first ultrasonic sensor 130a is located a distance of 9 mm from a floor surface and the second ultrasonic sensor 130b is located a distance of 12 mm from the floor surface.

In this case, if a waveform length of a first detection wave detected by the first ultrasonic sensor 130a is about 2.2 ms, it is determined that destructive interference has occurred in the first detection wave, and if a waveform length of a second detection wave detected by the second ultrasonic sensor 130b is about 3.5 ms, it is determined that constructive interference has occurred in the second detection wave.

Then, a material of a floor surface is determined in consideration of the fact that destructive interference has occurred in the first detection wave and constructive interference has occurred in the second detection wave.

Meanwhile, if a waveform length of a first detection wave detected by the first ultrasonic sensor 130a is about 1.8 ms, it is determined that constructive interference has occurred in the first detection wave, and if a waveform length of a second detection wave detected by the second ultrasonic sensor 130b is about 1.3 ms, it is determined that destructive interference has occurred in the second detection wave.

Then, a material of a floor surface is determined in consideration of the fact that constructive interference has occurred in the first detection wave and destructive interference has occurred in the second detection wave.

In this case, information about reference interference waveforms according to materials of a floor surface includes information representing that a material of a floor surface is a hard material when destructive interference has occurred in a first detection wave and constructive interference has occurred in a second detection wave, and that a material of a floor surface is a soft material when constructive interference has occurred in a first detection wave and destructive interference has occurred in a second detection wave.

Also, it is possible to store information about interference types and waveform lengths according to distances between the first ultrasonic sensor 130a and a floor surface, information about interference types and waveform lengths according to a distance between the second ultrasonic sensor 130b and the floor surface, and information about materials of the floor surface corresponding to interference types of detection waves detected by the first and second ultrasonic sensors 130a and 130b.

In this case, the robot cleaner detects distances to the floor surface and detection waves using the first and second ultrasonic sensors 130a and 130b, and determines a material of the floor surface based on the distances and the interference types of the detection waves.

Figure 12:
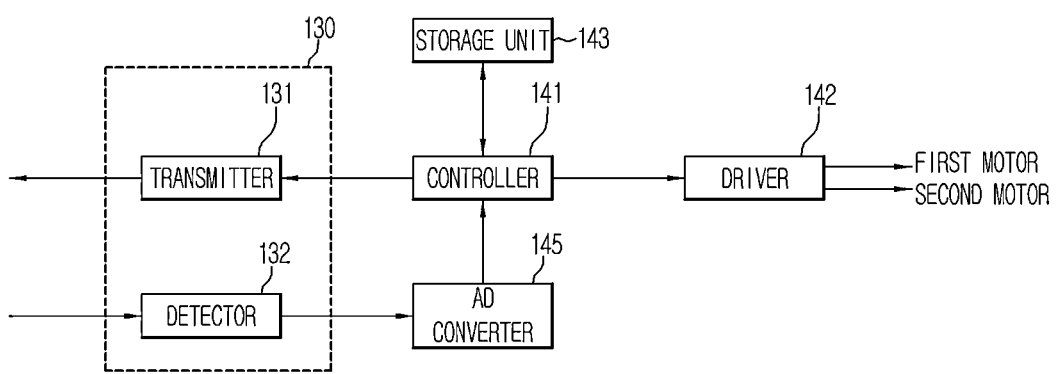
FIG. 12 is a block diagram illustrating a robot cleaner according to another embodiment of the present disclosure.

FIG. 12 is a block diagram illustrating a robot cleaner according to another embodiment of the present disclosure. Referring to FIG. 12, the robot cleaner includes an ultrasonic sensor 130, a controller 141, a driver 142, a storage unit 143, and an Analog-to-Digital (AD) converter 145.

The ultrasonic sensor 130 generates an ultrasonic wave, and outputs an ultrasonic detection wave if receiving an ultrasonic wave reflected from an external object. The ultrasonic sensor 130 includes a transmitter 131 and a detector 132.

The transmitter 131 and the detector 132 have been described above with reference to FIG. 6, and accordingly, detailed descriptions thereof will be omitted.

During traveling and cleaning, the controller 141 controls driving of the transmitter 131 and the detector 132, calculates an average amplitude of data detected by the detector 132 and converted by the AD converter 145, determines information about a floor surface based on the calculated average amplitude, and controls at least one of a cleaning mode and traveling based on the determined information of the floor surface.

Also, the controller 141 may calculate an average amplitude using an analog detection wave.

The cleaning mode may include a wet mode and a dry mode. In this case, the robot cleaner includes both a main brush and a rag, and performs cleaning using at least one of the main brush and the rag according to a cleaning mode.

In more detail, the controller 141 calculates an average amplitude of a detection wave based on data transferred from the AD converter 145, a tail length of the detection wave based on the average amplitude, and an average amplitude deviation of the detection wave, compares the average amplitude of the detection wave, the tail length of the detection wave, and the average amplitude deviation of the detection wave to predetermined reference ranges, respectively, and determines information about a floor surface according to the results of the comparison.

Alternatively, the controller 141 may determine information about a floor surface using a waveform length, an average amplitude, and an average amplitude deviation.

The information about the floor surface includes information about a material of the floor surface, which influences the mechanical properties of the floor surface, such as hardness, roughness, etc. of the floor surface, information about whether the object surface has been contaminated by liquid, information about whether an empty space exists, etc.

Also, the information about the floor surface further includes information about a location of a floor area with different mechanical properties from those of the balance of the floor surface.

For example, information about a location of a floor area may be information about a location of a carpet laid on a part of a floor surface to be cleaned when the remainder of the floor surface is covered with vinyl linoleum.

The average amplitude of the detection wave is an average value of amplitudes appearing from a time at which a reflection wave has been received to a time at which attenuation of the detection wave terminates. The amplitude of the detection wave is a voltage value.

The tail length of the detection wave is a waveform length of the detection wave when the detection wave has a value smaller than the average amplitude, and the average amplitude deviation of the detection wave is a deviation of the average amplitude.

The controller 141 determines a material of the floor surface according to a relative degree of hardness (i.e., whether relatively hard or soft) of the floor surface, whether the floor surface has been contaminated by liquid, and whether an empty space such as a gap or hole exists, determines avoidance traveling or continuous traveling based on the material of the floor surface, the contaminated state of the floor surface, and the existence of an empty space, controls driving of the first motors (121b of FIG. 2) according to the result of the determination to change a traveling direction and a traveling speed, and controls driving of the second motor (122c of FIG. 2) to change a cleaning mode.

If it is determined that the material of the floor surface is a soft material, the controller 141 may calculate a distance to the floor surface made of a soft material based on an oscillation time of an oscillation wave and a reception time of a reflection wave, determine a location of the floor surface based on the calculated distance, and control avoidance traveling before the robot cleaner arrives at the determined location of the floor surface.

The controller 141 may select reference data according to a distance between the floor surface and the ultrasonic sensor 130.

Meanwhile, if it is determined that an empty space exists or that liquid exists on the floor surface, the controller 141 may recognize the corresponding location of the floor surface and implement an avoidance traveling routine of the robot cleaner before the robot cleaner arrives at the recognized location of the floor surface.

The driver 142 has been described above with reference to FIG. 6, and accordingly, a detailed description thereof will be omitted.

The storage unit 143 stores a reference average amplitude range, a reference tail length range, and a reference average deviation range for a hard material, and a reference average amplitude range, a reference tail length range, and a reference average deviation range for a soft material.

Also, the storage unit 143 stores a reference average amplitude range for existence of liquid, and a reference average amplitude range, a reference tail length range, and a reference average deviation range for an empty space.

Also, reference data for information about a floor surface, stored in the storage unit 143, may change according to an installation height of the ultrasonic sensor 130. The installation height of the ultrasonic sensor 130 may be based on a distance to a floor surface, and may be pre-stored or calculated using a Time-Of-Flight (TOF) of an oscillation wave.

The AD converter 145 converts an analog voltage signal transferred from the detector 132 into digital data, and transfers the digital data to the controller 141.

The digital data converted by the AD converter 145 may include digital data of an oscillation wave, a reflection wave, and a composite wave appearing when the oscillation wave overlaps the reflection wave.

In the present embodiment, the AD converter 145 is used to convert an analog detection wave into a digital detection wave and then to calculate an average amplitude. It is, however, also possible to calculate an average amplitude of an analog detection wave using a waveform analyzer instead of the AD converter 145.

Figure 13:
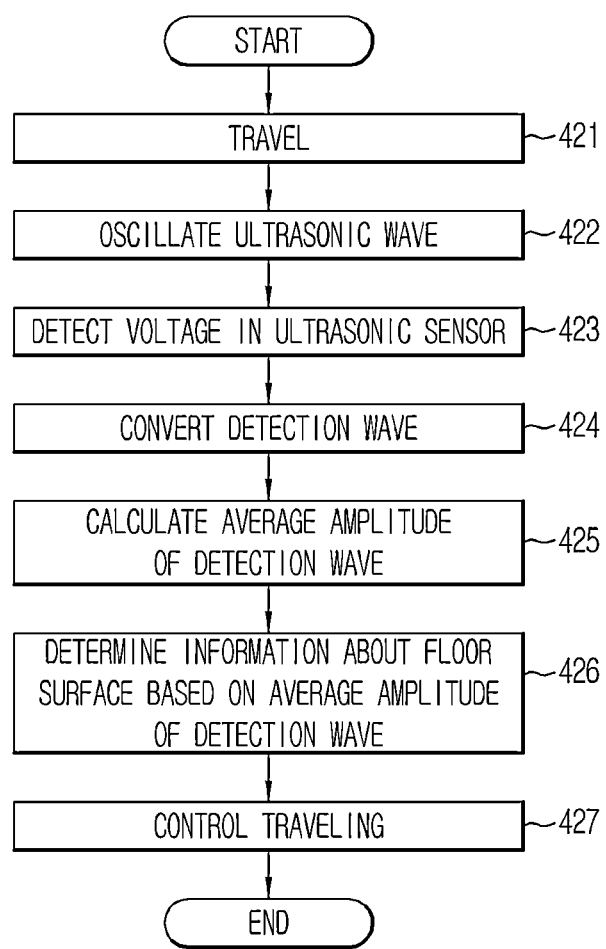
FIG. 13 is a flowchart illustrating a method of controlling the robot cleaner according to another embodiment of the present disclosure.

FIG. 13 is a flowchart illustrating a method of controlling the robot cleaner according to another embodiment of the present disclosure. Hereinafter, the method of controlling the robot cleaner will be described with reference to FIGS. 1, 2, 13, 14A to 14C, and 15.

If a cleaning command or a traveling command is received through the input unit 112, the robot cleaner drives the first motors 121b to rotate the wheels 121a, thereby traveling based on pre-stored map information (421), and drives the second motor 122c to rotate the main brush 122a, thereby performing cleaning.

During traveling and cleaning, the robot cleaner drives the ultrasonic sensor 130 to oscillate an ultrasonic wave toward a floor surface (422).

Thereafter, a reflection wave reflected from a floor surface is received by the ultrasonic sensor 130.

The robot cleaner detects a voltage signal generated in the ultrasonic sensor 130 upon oscillation and reception of the ultrasonic waves, amplifies the voltage signal to a predetermined magnitude, and then performs filtering for blocking noise corresponding to a low frequency band while passing only a high frequency band.

The voltage detected by a transmitter of the ultrasonic sensor 130 is a voltage generated by an oscillation wave, a reflection wave, and a composite wave. The voltage corresponds to a detection wave.

The composite wave is a waveform appearing when the oscillation wave overlaps the reflection wave or a waveform appearing when an aftershock overlaps the reflection wave.

Then, the robot cleaner converts the voltage of the detection wave into digital data (424), and determines information about a floor surface based on the digital data.

Also, the robot cleaner may subtract a voltage value of the oscillation wave from the voltage value of the detection wave to extract a voltage value of the reflection wave, and determine information about a floor surface using the voltage value of the reflection wave.

Determination on the information about the floor surface based on the detection wave will be described in more detail, below.

The robot cleaner detects a time at which the reflection wave in the composite wave is received and a time at which attenuation of the reflection wave terminates, and calculates an average amplitude of the detection wave in a time period between the detected times.

Alternatively, the robot cleaner may determine information about the floor surface using an average amplitude of only the composite wave in the detection wave.

The average amplitude of the detection wave varies depending on a material of the floor surface, whether a liquid exits on the floor surface, and whether an empty space such as a gap or a hole exists. This will be described in more detail with reference to FIGS. 14A to 14C and 15, below.

Figure 14A:
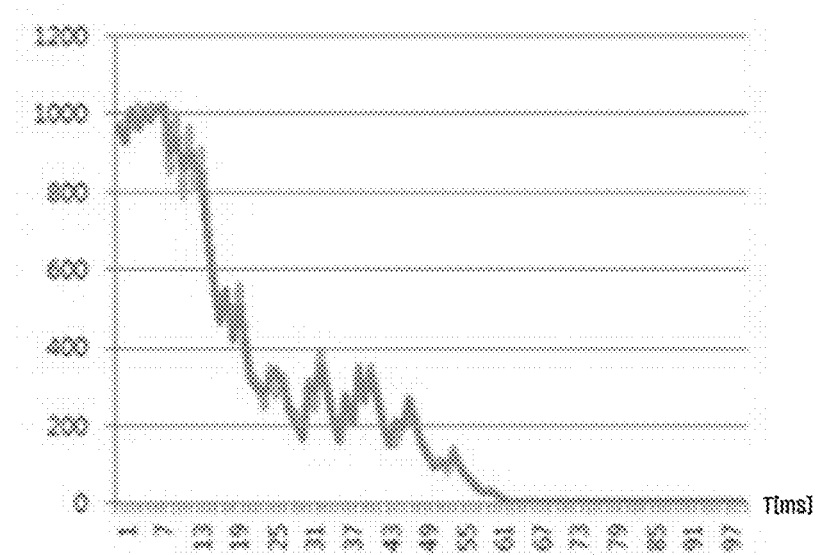
FIGS. 14A, 14B, and 14C are graphs showing examples of digital signals generated according to floor materials, converted from voltage signals output from an ultrasonic sensor of the robot cleaner according to another embodiment of the present disclosure.
Figure 14B:
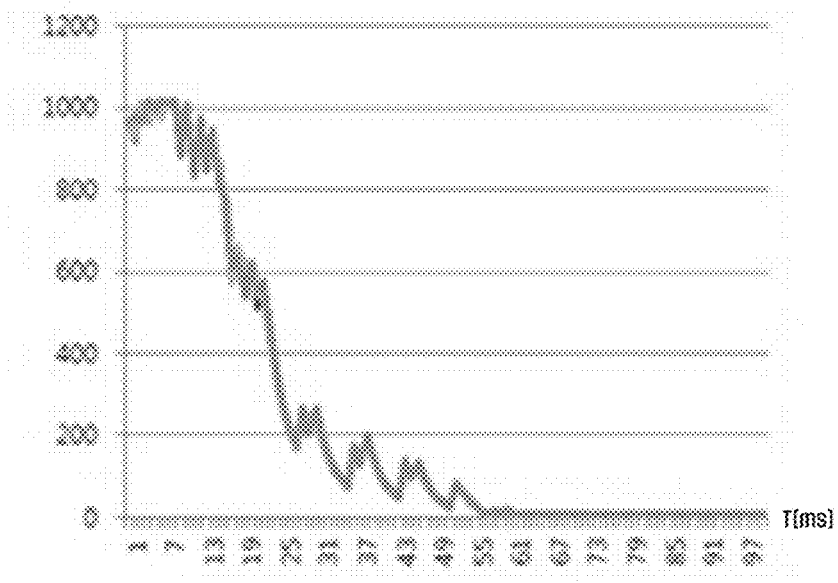
Figure 14C:
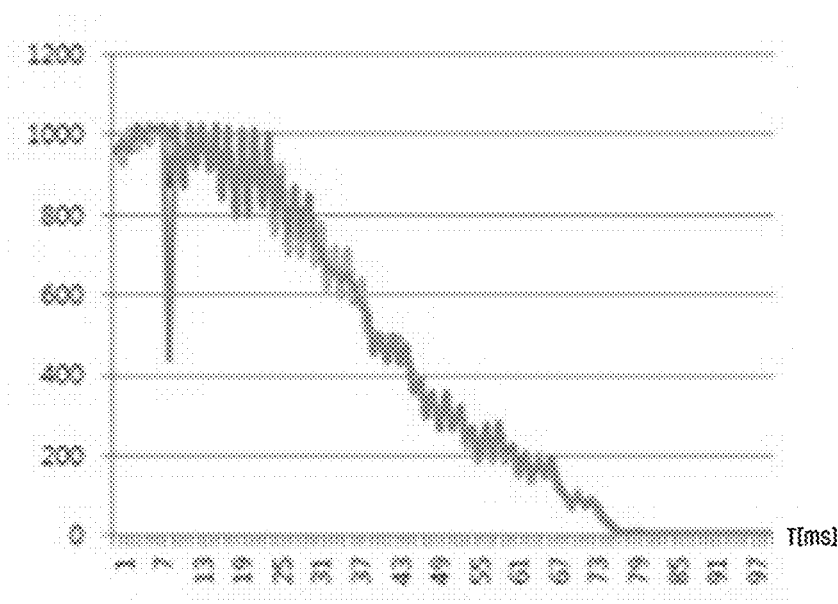

FIGS. 14A to 14C are graphs showing examples of detection waves detected over time by the robot cleaner according to another embodiment of the present disclosure, the detection waves corresponding to information about floor surfaces, wherein FIG. 14A is a graph showing a detection wave generated by a reflection wave reflected from a floor surface made of a hard material, FIG. 14B is a graph showing a detection wave generated by a reflection wave reflected from a floor surface made of a soft material, and FIG. 14C is a graph showing a detection wave generated by a reflection wave reflected from a floor surface made of a hard material and having liquid thereon. In FIGS. 14A to 14C, the vertical axis represents voltage values converted into digital signal values.

Referring to FIGS. 14A to 14C, the floor surface made of the hard material, the floor surface made of the soft material, and the floor surface having liquid thereon have different properties from each other.

That is, in the case in which the floor surface is made of the hard material, a waveform length of the detection wave is 61 ms, in the case in which the floor surface is made of the soft material, a waveform length of the detection wave is 55 ms, and in the case in which the floor surface has liquid thereon, a waveform length of the detection wave is 77 ms.

The reason why the detection wave has a long waveform length when liquid exist on the floor surface is because a reflection wave reflected from the interface between the floor surface and the liquid overlaps an oscillation wave or aftershock to increase vibration energy.

As such, based on a difference in a waveform length according to a distance between the ultrasonic sensor 130 and a floor surface, additional information, such as a material of the floor surface or whether liquid exists on the floor surface, may be acquired.

Also, an average amplitude for a time period between a time at which attenuation of a detection wave starts and a time at which the attenuation of the detection wave terminates is different according to information about a floor surface.

That is, the greater average amplitudes are calculated in an order of the case in which liquid exists on a floor surface and the case in which a material of a floor surface is a solid material. Also, the greater average amplitude is calculated in the case in which a floor surface is made of a hard material compared to the case in which a floor surface is made of a soft material.

Reference average amplitude ranges of a detection wave corresponding to information about a floor surface have been acquired by a test and are pre-stored.

In other words, a reference average amplitude range for a hard material, a reference average amplitude range for a soft material, a reference average amplitude range for a liquid surface, and a reference average amplitude range for an empty space are stored in advance in the storage unit 143.

Accordingly, the robot cleaner compares the calculated average amplitude to the plurality of reference average amplitude ranges, and determines which one of the reference average amplitude ranges the calculated average amplitude belongs to, thereby determining that the information about the floor surface corresponds to the case in which a floor surface is made of a hard material, the case in which a floor surface is made of a soft material, or the case in which liquid exists on the floor surface (426).

Then, the robot cleaner controls driving of the first motors 121b based on the result of the determination, thereby controlling traveling. Also, the robot cleaner may control driving of the first motors 121b and the second motor 122c to change a cleaning mode.

An example of controlling traveling of the robot cleaner will be described as follows.

If liquid exists on a floor surface or if the floor surface is made of a soft material, the robot cleaner changes RPMs of the first motors 121b to change a traveling direction, thereby performing avoidance traveling, and if the floor surface is made of a hard material, the robot cleaner performs continuous traveling based on map information.

Then, an example of changing a cleaning mode of the robot cleaner will be described as follows.

If it is determined that a floor surface is made of a soft material, the robot cleaner determines that a carpet is laid on the floor surface, and sets the cleaning mode to a carpet mode.

If the robot cleaner includes a dry mode and a wet mode, the robot cleaner sets a cleaning mode to the wet mode when it is determined that liquid exist on a floor surface, to remove the liquid, and if liquid is no longer found on the floor surface, the robot cleaner again sets the cleaning mode to the dry mode.

Also, as shown in FIGS. 14A to 14C, in consideration of the fact that a difference between reference average amplitudes in the cases of a floor surface made of a hard material and a floor surface made of a soft material is not great, by determining information about a floor surface using tail lengths and average deviations based on average amplitudes of detection waves, accuracy in determining information about a floor surface may be improved. At this time, it is also possible to determine whether the floor surface is an empty space.

A relationship between a tail length and an average deviation according to materials of a floor surface will be described with reference to FIG. 15, below.

Figure 15:
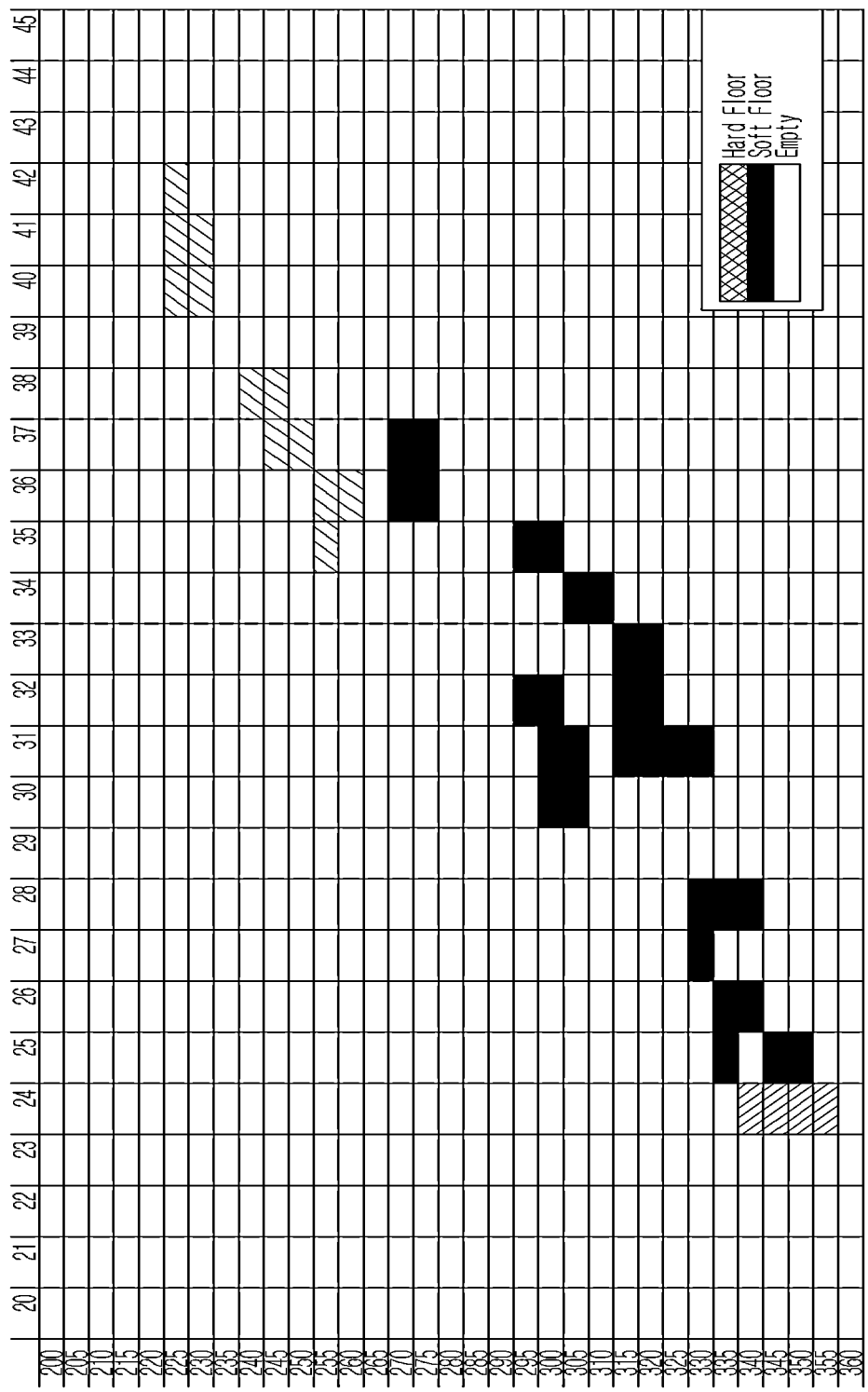
FIG. 15 illustrates examples of reference data ranges corresponding to information about a floor surface, which are used in the robot cleaner according to another embodiment of the present disclosure to determine the information about the floor surface.

FIG. 15 illustrates examples of reference data ranges corresponding to information about a floor surface, which are used for the robot cleaner according to another embodiment of the present disclosure to determine the information about the floor surface.

As illustrated in FIG. 15, reference tail length ranges and reference average deviation ranges for a hard floor, a soft floor, and an empty space have been acquired by a test and set.

As seen from FIG. 15, greater average deviations are obtained in an order of the empty space, the soft floor, and the hard floor.

Also, longer tail lengths are obtained in an order of the hard floor, the soft floor, and the empty space.

Also, in the hard and soft floors, the longer tail lengths, the smaller average deviations, and in the empty floor, a constant tail length is maintained, and an average deviation is also maintained in a constant range.

That is, the robot cleaner may determine information about a floor surface using an average deviation and a tail length based on an average amplitude. This will be described in more detail, below.

The robot cleaner calculates a tail length which corresponds to an area of a detection wave wherein an amplitude is smaller than an average amplitude of the detection wave, compares the calculated tail length to a plurality of reference tail length ranges, determines which one of the reference tail length ranges the calculated tail length corresponds to, and determines whether the floor surface is a floor surface made of a hard material, a floor surface made of a soft material, or an empty space.

Also, the robot cleaner calculates an average deviation for an average amplitude, compares the calculated average deviation to a plurality of reference average deviation ranges, determines which one of the reference average deviation ranges the calculated average deviation belongs to, and determines whether the floor surface is a floor surface made of a hard material, a floor surface made of a soft material, or an empty space.

As such, since accuracy of information about a floor surface is improved so that the robot cleaner can decide a traveling direction and automatically set a cleaning mode based on the information about the floor surface, the efficiency of cleaning may be improved, resulting in high consumer satisfaction.

Hereinafter, the configuration of the robot cleaner according to an embodiment of the present disclosure will be described with reference to FIG. 6.

Referring to FIG. 6, the ultrasonic sensor 130 includes the transmitter 131 and the detector 132, as described above. Since the transmitter 131, the detector 132, and the driver 142 have been described above, detailed descriptions thereof will be omitted.

The controller 141 controls a cleaning mode and driving of the transmitter 131 and the detector 132, determines information about a floor surface based on the result of waveform analysis of a detection wave transferred from the waveform analyzer 144, and controls at least one of the cleaning mode and traveling based on the information about the floor surface.

The result of the waveform analysis includes at least one among a maintenance time period for which a voltage corresponding to an oscillating wave is maintained from a time at which a detection wave is received, a first time at which the waveform of the detection wave starts to attenuate, a second time at which the waveform attenuation of the detection wave terminates, and a gradient corresponding to a voltage difference over time between a voltage at the first time and a voltage at the second time.

That is, the maintenance time period for which the voltage corresponding to the oscillation wave is maintained is a time period from a time at which the oscillation wave oscillates to the first time.

In more detail, if the controller 141 receives a maintenance time period for which a voltage corresponding to an oscillation wave is maintained, a first time at which the waveform of a detection wave starts to attenuate, a second time at which the waveform attenuation of the detection wave terminates, a gradient corresponding to a voltage difference over time between a voltage at the first time and a voltage at the second time from the waveform analyzer 144, the controller 141 determines information about a floor surface by comparing the maintenance time period, the first time, the second time, and the gradient to a plurality of reference maintenance time periods, a plurality of first reference times, a plurality of second reference times, and a plurality of reference gradients, respectively.

The plurality of reference maintenance time periods, the plurality of first reference times, the plurality of second reference times, and the plurality of reference gradients are reference data set in advance according to information about a floor surface.

Information about a floor surface includes information about a material of a floor surface, which influences the mechanical properties of the floor surface, such as hardness, roughness, etc. of the floor surface, information about whether the floor surface has been contaminated by liquid, the location of a carpet or pad laid on the floor surface, etc.

That is, determining information about a floor surface is to determine whether the floor surface is a smooth, hard surface or a rough, soft surface or whether contaminants such as liquid exist on the floor surface.

The controller 141 determines whether to perform avoidance traveling or continuous traveling according to the determined information about the floor surface, controls driving of the first motors (121*b* of FIG. 2) according to the result of the determination to change a traveling direction and a traveling speed, and controls driving of the second motor (122*c* of FIG. 2) to change a cleaning mode.

Here, the cleaning mode includes a hard mode and a soft mode which are classified according to a material of a floor surface. When a cleaning mode changes, a sucking force and a rotation speed of the main brush (122*a* of FIG. 2) change accordingly.

Also, the cleaning mode may further include a wet mode and a dry mode.

The storage unit 143 stores a reference maintenance time period, a first reference time, a second reference time, and a first gradient for a hard floor, and a reference maintenance time period, a first reference time, a second reference time, and a first gradient for a soft floor. The first reference times, the second reference times, and the reference gradients have predetermined error ranges.

Also, the storage unit 143 further stores a reference maintenance time period, a first reference time, a second reference time, and a reference gradient for a liquid surface when water exists on a floor surface.

The waveform analyzer 144 analyzes the waveform of an analog detection wave transferred from the detector 132.

The waveform analyzer 144 detects a detection wave and compares the detection wave to a threshold value, to thereby extract feature points, and transfers information about the feature points to the controller 141.

The feature points correspond to the first time at which the detection wave start to attenuate and the second time at which the attenuation of the detection wave terminates, and the maintenance time period and the gradient may be detected based on information about the first and second times.

In other words, the waveform analyzer 144 detects a maintenance time period from the time at which the detection wave has been received to the first time, and detects a gradient at which the waveform of the detection wave attenuates based on a time period between the first and second times and a change in a voltage between the first and second times.

Also, the waveform analyzer 144 may detect only feature points, and the controller 141 may calculate a maintenance time and a gradient using information about the feature points.

Hereinafter, a method of controlling the robot cleaner according to the present embodiment will be described with reference to FIG. 16.

Figure 16:
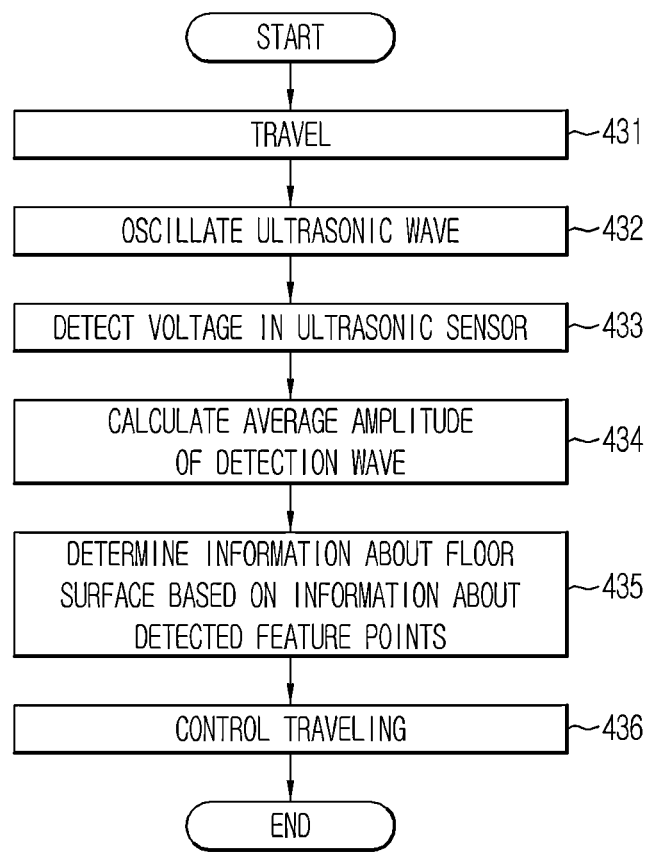
FIG. 16 is a flowchart illustrating a method of controlling a robot cleaner according to another embodiment of the present disclosure.

FIG. 16 is a flowchart illustrating a method of controlling the robot cleaner, and the method of controlling the robot cleaner will be described with reference to FIGS. 1, 2, 16 and 17.

If a cleaning command or a traveling command is received through the input unit 112, the robot cleaner drives the first motors 121b to rotate the wheels 121a, thereby traveling based on pre-stored map information (431), and also drives the second motor 122c to rotate the main brush 122a, thereby performing cleaning.

During traveling and cleaning, the robot cleaner drives the ultrasonic sensor 130 to oscillate ultrasonic waves toward a floor surface (432).

Thereafter, a reflection wave reflected from the floor surface is received by the ultrasonic sensor 130.

Then, the robot cleaner detects a voltage signal according to the oscillation and reception of the ultrasonic wave (433), amplifies the detected voltage signal to a predetermined magnitude, and performs filtering for blocking noise corresponding to a low frequency band and passing only a high frequency band.

Then, the robot cleaner analyzes a detection wave. This will be described with reference to FIG. 18, later.

Figure 17:
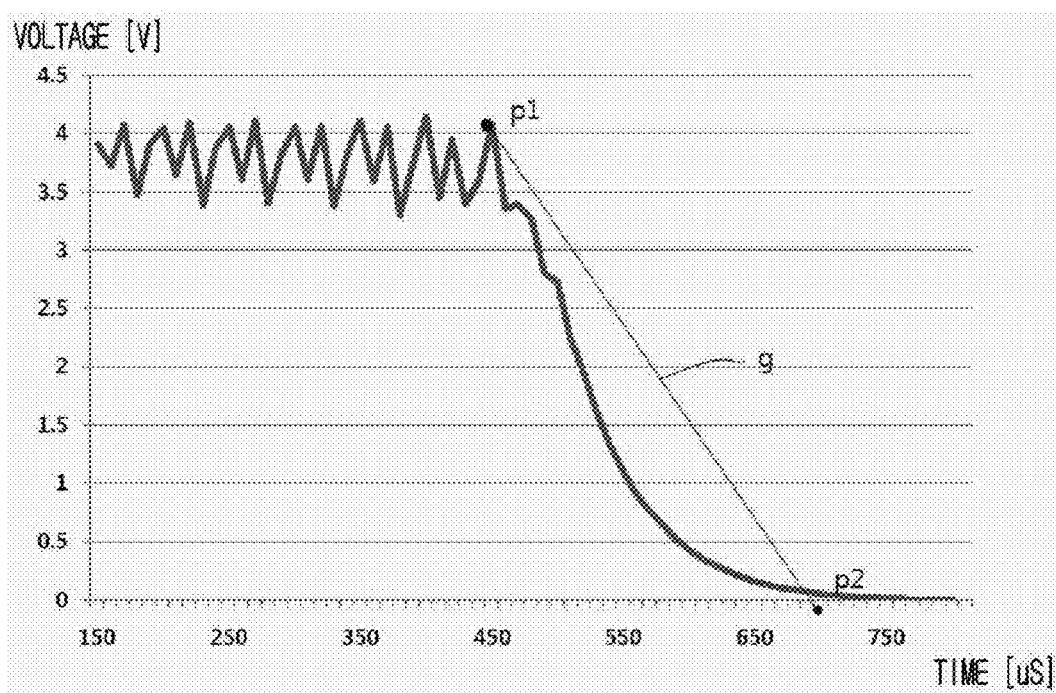
FIG. 17 is a graph for describing detection of feature points in the method of controlling the robot cleaner according to another embodiment of the present disclosure.

FIG. 17 is a graph for describing detection of feature points in the method of controlling the robot cleaner according to another embodiment of the present disclosure;

As illustrated in FIG. 17, the ultrasonic sensor 130 continues to oscillate even after an oscillation wave is transferred, and if a reflection wave is received while the ultrasonic sensor 130 oscillates, the reflection wave overlaps the oscillation wave so that destructive interference or constructive interference occurs, and then the resultant wave starts to attenuate.

The robot cleaner detects a detection wave and compares the detection wave to a threshold value to detect feature points p1 and p2 at a first time at which the detection wave starts to attenuate and at a second time at which the attenuation of the detection wave terminates (434).

Also, the robot cleaner calculates a time period between the first and second times, and a gradient g corresponding to a voltage change over time between a voltage at the first time and a voltage at the second time. The calculated gradient is a gradient at which the waveform of the detection wave attenuates.

Also, the robot cleaner detects a maintenance time period between a time at which the detection wave has been received and the first time. Also, the robot cleaner may detect a time period between a time at which a reflection wave in the detection wave has been received and the first time, as a maintenance time period.

Then, the robot cleaner determines information about a floor surface using at least one piece of information among the maintenance time period, the first time, the second time, and the gradient which are information about the detected feature points (435).

In more detail, the robot cleaner compares the detected first time to a plurality of first reference times, respectively, searches for a first reference time matching the detected first time in the plurality of first reference times, and determines information about a floor surface corresponding to the detected first reference time.

Also, the robot cleaner may search for a second reference time, a reference gradient, and a reference maintenance time period corresponding to the detected second time, the detected gradient, and the detected maintenance time period, respectively, in order to improve accuracy in determining information about a floor surface.

That is, the robot cleaner compares the detected second time to a plurality of second reference times, searches for a second reference time matching the detected second time in the plurality of second reference times, determines information about a floor surface corresponding to the found second reference time, calculates a gradient corresponding to a voltage difference over time between a voltage at the first time and a voltage at the second time, compares the calculated gradient to a plurality of reference gradients, respectively, searches for a reference gradient corresponding to the calculated gradient in the plurality of reference gradients, and determines information about a floor surface corresponding to the found reference gradient.

Also, the robot cleaner compares the detected maintenance time period to a plurality of reference maintenance time periods, respectively, searches for a reference maintenance time period corresponding to the detected maintenance time period in the plurality of reference maintenance time periods, and determines information about a floor surface corresponding to the found reference maintenance time period.

The information about the floor surface includes a material of the floor surface, whether liquid exists on the floor surface, etc.

Then, the robot cleaner controls driving of the first motors 121b based on the result of the determination to control traveling (436). Also, the robot cleaner may control the first motors and the second motor 121b and 122c based on the result of the determination to thereby change a cleaning mode.

An example of controlling traveling of the robot cleaner will be described as follows.

If a material of a floor surface is a soft material or if liquid exists on the floor surface, the robot cleaner changes RPMs of the first motors 121b to change a traveling direction, thereby performing avoidance traveling, and if a material of a floor surface is a hard material, the robot cleaner performs continuous traveling based on map information.

An example of changing a cleaning mode of the robot cleaner will be described as follows.

If a material of a floor surface is a soft material, the robot cleaner determines that a carpet is laid on the floor surface, and sets the cleaning mode to a carpet mode.

If the robot cleaner includes a dry mode and a wet mode, the robot cleaner sets a cleaning mode to the wet mode when it is determined that liquid exist on a floor surface, to remove the liquid, and if liquid is no longer found on the floor surface, the robot cleaner again sets the cleaning mode to the dry mode.

A configuration of the robot cleaner according to the present embodiment will be described with reference to FIG. 6. Referring to FIG. 6, the robot cleaner includes the ultrasonic sensor 130, the controller 141, the driver 142, the storage unit 143, and the waveform analyzer 144. The ultrasonic sensor 130 includes the transmitter 131 and the detector 132, and since the transmitter 131, the detector 132, and the driver 142 have been described above, detailed descriptions thereof will be omitted.

Referring to FIGS. 1, 2, and 6, if a cleaning command or a traveling command is received through the input unit 112, the controller 141 controls at least one of a cleaning mode and a traveling mode based on pre-stored map information, controls driving of the transmitter 131 and the detector 132, determines information about a floor surface based on the result of waveform analysis on a detection wave, transferred from the waveform analyzer 141, and controls at least one of the cleaning mode and traveling based on the determined information about the floor surface.

The waveform analysis is to detect an oscillation wave, a reflection wave, and an echo wave from the detection wave, to detect times at which the oscillation wave, the reflection wave, and the echo wave have been generated, and the intensities of the oscillation wave, the reflection wave, and the echo wave, and to detect an attenuation rate between echo waves.

In more detail, if data about times at which an oscillation wave, a reflection wave, and an echo wave have been generated, the intensities of the oscillation wave, the reflection wave, and the echo wave, and an attenuation rate between echo waves is received from the waveform analyzer 144, the controller 141 compares the received data to reference data about floor materials, respectively, to determine information about a floor surface.

The information about the floor surface includes information about a material of a floor surface, which influences the mechanical properties of the floor surface, such as hardness, elasticity, roughness, etc. of the floor surface, the location of a carpet or pad laid on the floor surface, etc.

The controller 141 determines whether to perform avoidance traveling or continuous traveling based on the determined information about the floor surface, controls driving of the first motors (121b of FIG. 2) based on the result of the determination to change a traveling direction and a traveling speed, and also controls driving of the second motor (121c of FIG. 2) to change a cleaning mode.

Here, the cleaning mode includes a hard mode and a soft mode which are classified according to a material of a floor surface. When a cleaning mode changes, a sucking force and a rotation speed of the main brush (122a of FIG. 2) change accordingly.

The storage unit 143 stores first reference intensities of a reflection wave according to floor materials, numbers of reference echo waves according to floor materials, a second reference intensity for each echo wave, and a reference attenuation rate.

Also, different values of reference data are stored according to distances between the ultrasonic sensor 130 and a floor surface.

The waveform analyzer 144 analyzes the waveform of an analog detection wave transferred from the detector 132.

The waveform analyzer 144 detects an oscillation wave, a reflection wave, and an echo wave from the detection wave, detects information about the reflection wave, such as the intensity of the detected reflection wave, the number of echo waves, an attenuation rate for each echo, etc., and transmits the information about the reflection wave to the controller 141.

The waveform analyzer 144 may detect the echo wave using a peak detection algorithm.

Figure 18:
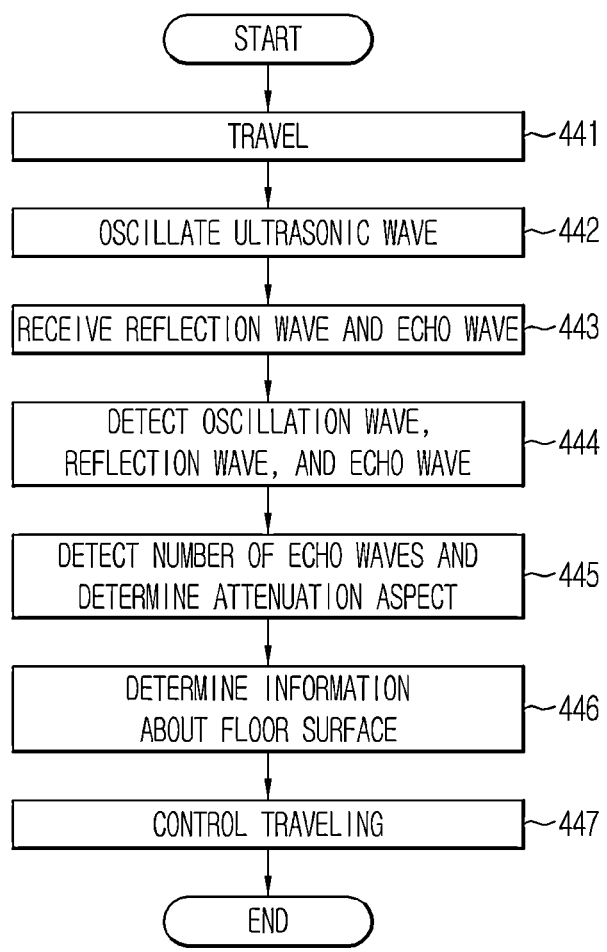
FIG. 18 is a flowchart illustrating a method of controlling a robot cleaner according to another embodiment of the present disclosure.

FIG. 18 is a flowchart illustrating a method of controlling a robot cleaner according to another embodiment of the present disclosure. The method of controlling the robot cleaner will be described with reference to FIGS. 1, 2, 18, 19, and 20.

If a cleaning command or a traveling command is received through the input unit 112, the robot cleaner drives the first motors 121b to rotate the wheels 121a, thereby traveling based on pre-stored map information (441), and also drives the second motor 122c to rotate the main brush 122a, thereby performing cleaning.

During traveling and cleaning, the robot cleaner drives the ultrasonic sensor 130 to oscillate an ultrasonic wave toward a floor surface (442).

If a reflection wave reflected from the floor surface is received, the robot cleaner detects a voltage signal generated by the received reflection wave, and if the reflection wave again oscillates toward the outside by oscillation of the ultrasonic sensor 130, then is reflected from the floor surface, and then received as an echo wave by the ultrasonic sensor 130, the robot cleaner detects a voltage signal generated by the echo wave.

As such, if a reflection wave and an echo wave are received by the ultrasonic sensor 130 (443), the robot cleaner detects voltage signals generated by the received reflection wave and echo wave, amplifies the detected voltage signals to predetermined magnitudes, and then performs filtering for blocking noise corresponding to a low frequency band and passing only a high frequency band.

The detected voltage signals are voltage signals generated by an oscillation wave, a reflection wave, a composite wave appearing when the oscillation wave overlaps the reflection wave, and an echo wave.

Then, the robot cleaner detects an oscillation wave, a reflection wave, and an echo wave from a detection wave (444), and determines an attenuation aspect, such as the intensities of the oscillation wave, the reflection wave, and the echo wave, a time at which the echo wave has been generated, an attenuation rate of the echo wave, etc. (445).

That is, the robot cleaner calculates a distance between the ultrasonic sensor 130 and the floor surface based on a TOF of an oscillation wave corresponding to a time period between a time at which the oscillation wave has oscillated and a time at which the reflection wave has been received.

Also, the robot cleaner estimates a time at which the reflection wave has been received based on the time at which the oscillation wave has oscillated and an attenuation aspect of a composite wave.

Then, the robot cleaner calculates an amplitude of the reflection wave in consideration of the magnitude of the oscillation wave in the composite wave, thereby detecting an intensity of the reflection wave.

During traveling, the robot cleaner may determine whether a carpet is laid on the floor surface by determining whether a distance between the ultrasonic sensor 130 and the floor surface changes, and select reference data corresponding to an actual distance between the floor surface and the ultrasonic sensor 130 from among reference data according to distances between the ultrasonic sensor 130 and a floor surface.

Then, the robot cleaner compares the intensity of the detected reflection wave to first reference intensities according to floor materials, searches for a first reference intensity matching the intensity of the detected reflection wave in the first reference intensities, and determines a floor material corresponding to the found first reference intensity.

This will be described with reference to FIG. 19, below.

Figure 19:
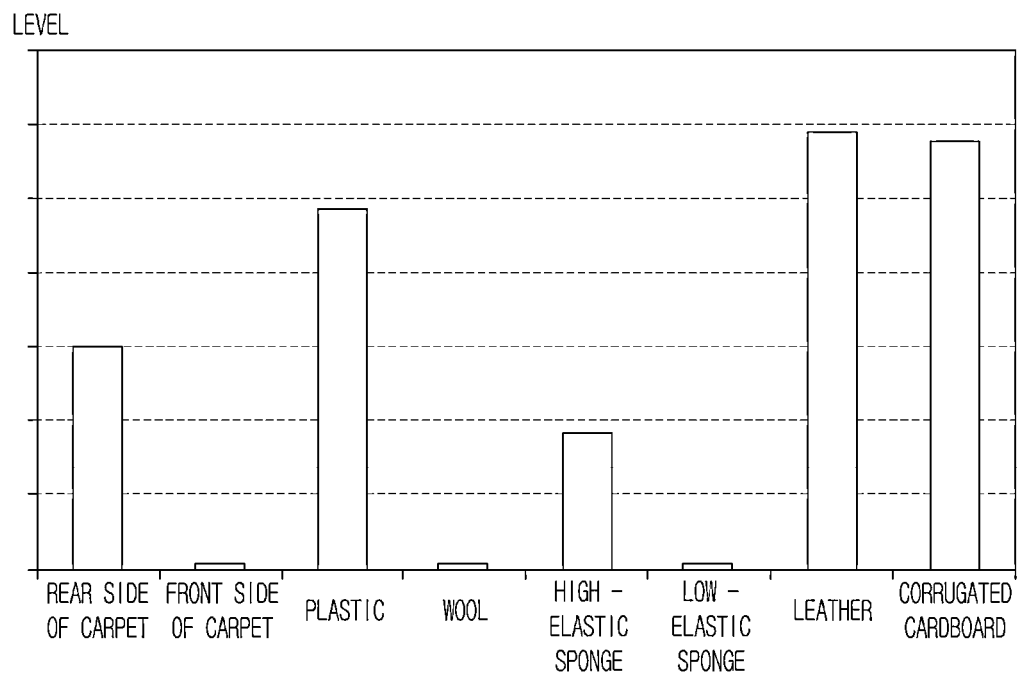
FIG. 19 is a graph showing intensities of reflection waves according to floor materials, detected by the robot cleaner according to another embodiment of the present disclosure.

FIG. 19 is a graph showing intensities of reflection waves according to floor materials. As illustrated in FIG. 19, the intensities of reflection waves are different according to floor materials.

In more detail, floor materials having a smooth, hard, high-elastic surface, such as the rear side of a carpet, plastic, high-elastic sponge-like material, leather, and corrugated cardboard, generate reflection waves having greater intensities, and floor materials having an uneven, rough, low-elastic surface, such as the front side of a carpet, wool, and low-elastic sponge-like material, generate reflection waves having smaller intensities.

Also, the floor materials having an even, rough, and low-elastic surface create a greater phase delay.

The robot cleaner may determine information about a floor surface based on at least one of an oscillation wave, an intensity of a reflection wave, a time at which an echo wave has been generated, a number of echo waves, and an attenuation rate of each echo wave (446). This will be described with reference to FIG. 20.

Figure 20A:
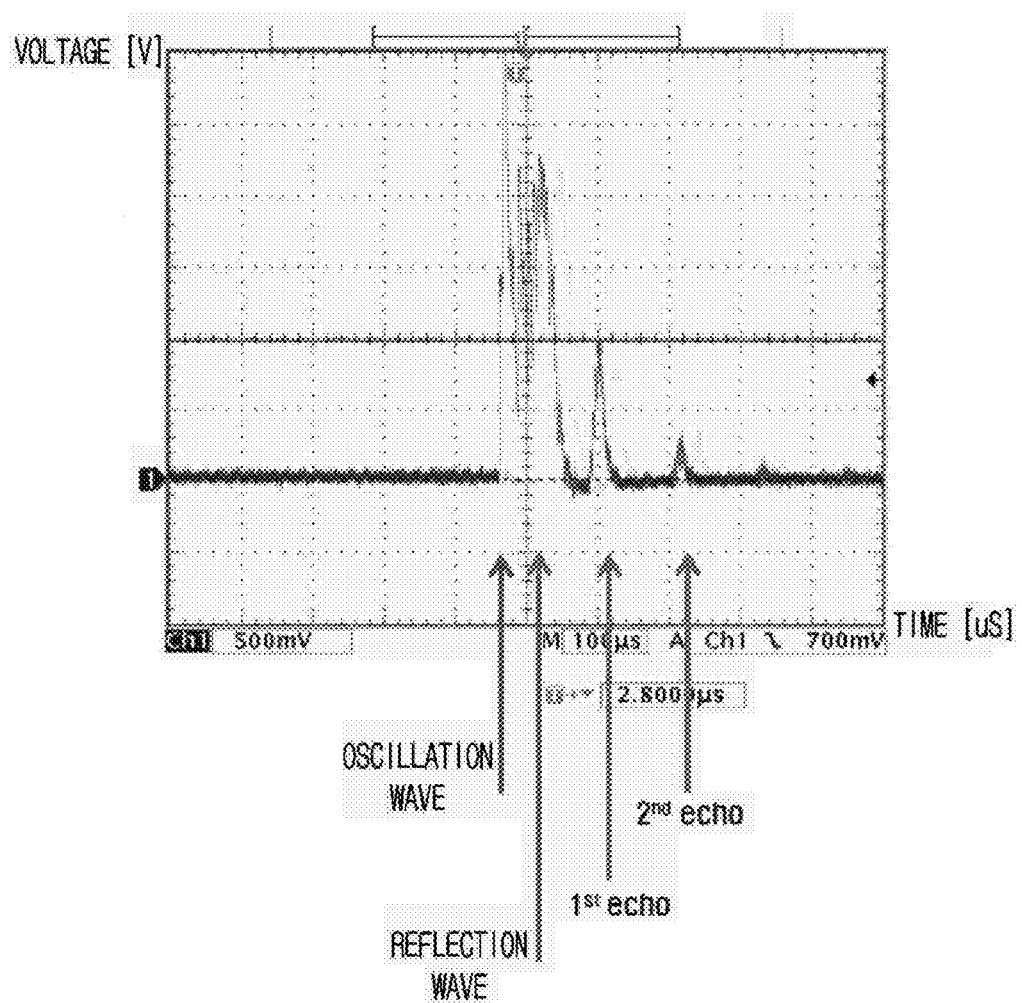
FIGS. 20A, 20B, and 20C are graphs showing oscillation waves, reflection waves, and echo waves according to floor materials, detected by the robot cleaner according to another embodiment of the present disclosure.
Figure 20B:
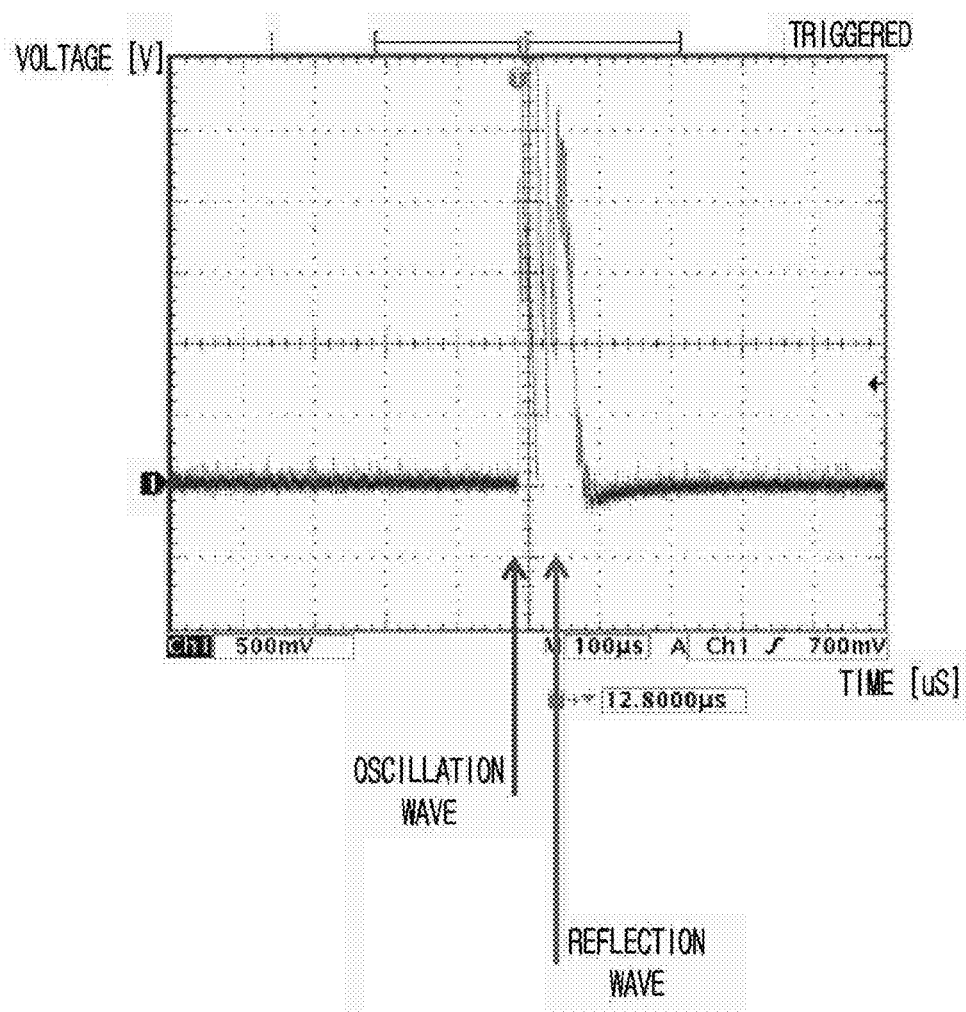
Figure 20C:
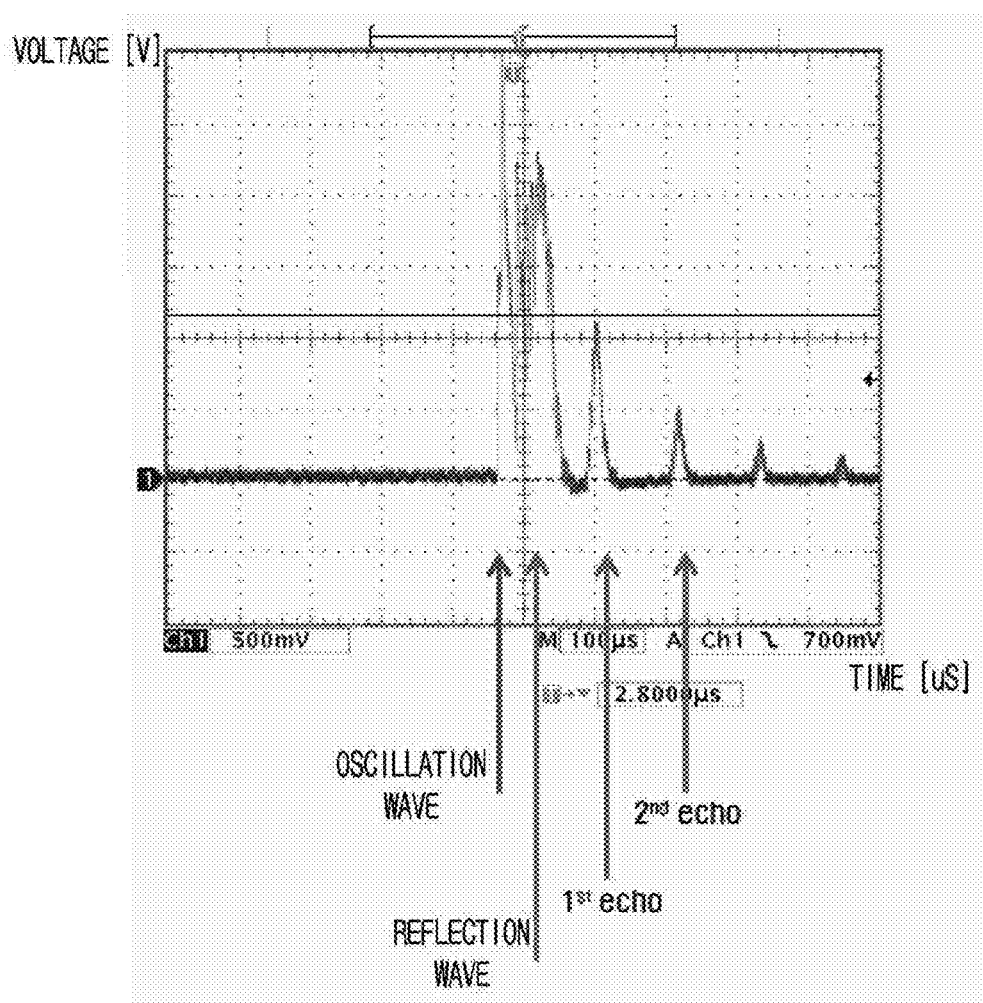

FIGS. 20A to 20C are graphs showing oscillation waves, reflection waves, and echo waves according to floor materials, detected by the robot cleaner according to another embodiment of the present disclosure.

FIG. 20A is a graph showing an oscillation wave, a reflection wave, and a first echo wave with respect to a smooth floor surface, FIG. 20B is a graph showing an oscillation wave and a reflection wave with respect to a rough floor surface, and FIG. 20C is a graph showing an oscillation wave, a reflection wave, a first echo wave, a second echo wave with respect to a reflection surface made of paper.

As illustrated in FIGS. 20A to 20C, a reflection wave received by the ultrasonic sensor 130 repeatedly oscillates toward and is again reflected against a floor surface when the floor surface is smooth, more times than when the floor surface is uneven.

Also, as illustrated in FIGS. 20A to 20C, an intensity of a reflection wave is great when a floor surface is smooth. Meanwhile, if a floor surface is soft and rough, an intensity of a reflection wave is great, but an echo wave little appears.

Referring to FIGS. 20A and 20C, intensities of echo waves are different according to an elasticity of a floor surface.

As such, the robot cleaner compares a number of echo waves to one or more reference numbers of echo waves according to floor materials, searches for a number of reference echo waves matching the number of echo waves in the reference numbers of echo waves, and determines a floor material corresponding to the determined number of reference echo waves.

Also, the robot cleaner calculates a first attenuation rate between the reflection wave and the first echo wave, and a second attenuation rate between the first and second echo waves, and determines a floor material based on at least one of the first and second attenuation rates.

That is, the robot cleaner compares the first attenuation rate to a plurality of first reference attenuation rates, searches for a first reference attenuation rate matching the first attenuation rate in the plurality of first reference attenuation rates, and determines a floor material corresponding to the found first reference attenuation rate.

Also, the robot cleaner compares the second attenuation rate to a plurality of second reference attenuation rates, searches for a second reference attenuation rate matching the second attenuation rate in the plurality of second reference attenuation rates, and determines a floor material corresponding to the determined first reference attenuation rate.

That is, the robot cleaner may determine material information, such as roughness of the floor surface, based on an oscillation wave, a reflection wave, and an echo wave.

Then, the robot cleaner controls driving of the first motors 121b based on the result of the determination to control traveling (447). Also, the robot cleaner controls driving of the first motors 121b and the second motor 122c based on the result of the determination to change a cleaning mode.

An example of controlling traveling of the robot cleaner will be described as follows.

If it is determined that a floor surface is rough and soft, the robot cleaner changes RPMs of the plurality of first motors 121b to change a traveling direction, thereby performing avoidance traveling, and if it is determined that the floor surface is smooth and hard, the robot cleaner performs continuous traveling based on map information.

Then, an example of changing a cleaning mode of the robot cleaner will be described as follows.

If it is determined that a floor surface is rough and soft, the robot cleaner determines that a carpet is laid on the floor surface, and sets a cleaning mode to a carpet mode.

According to embodiments as described above, the robot cleaner may be prevented from colliding with furniture, etc., getting struck by an object present on a floor surface, falling into a hole, or the like.

In addition, since the robot cleaner can select a cleaning mode according to a state or material of a floor to be cleaned, the robot cleaner may perform through cleaning while avoiding a contaminated area or an empty space so that breakdown due to collision with objects can be prevented.

The methods according to the above-described example embodiments may be recorded in non-transitory computer-readable media including program instructions to implement various operations embodied by a computer. The media may also include, alone or in combination with the program instructions, data files, data structures, and the like. The program instructions recorded on the media may be those specially designed and constructed for the purposes of the example embodiments, or they may be of the kind well-known and available to those having skill in the computer software arts. The media may also include, alone or in combination with the program instructions, data files, data structures, and the like. Examples of non-transitory computer-readable media include magnetic media such as hard disks, floppy disks, and magnetic tape; optical media such as CD ROM discs and DVDs; magneto-optical media such as optical discs; and hardware devices that are specially configured to store and perform program instructions, such as read-only memory (ROM), random access memory (RAM), flash memory, and the like.

Examples of program instructions include both machine code, such as produced by a compiler, and files containing higher level code that may be executed by the computer using an interpreter. The described hardware devices may be configured to act as one or more software modules in order to perform the operations of the above-described embodiments, or vice versa. Any one or more of the software modules described herein may be executed by a dedicated hardware-based computer or processor unique to that unit or by a hardware-based computer or processor common to one or more of the modules. The described methods may be executed on a general purpose computer or processor or may be executed on a particular machine such as the robot cleaning apparatus described herein.

Although a few embodiments of the present disclosure have been shown and described, it would be appreciated by those skilled in the art that changes may be made in these embodiments without departing from the principles and spirit of the disclosure, the scope of which is defined in the claims and their equivalents.

What is claimed is:

1. A robot cleaner comprising:
   a traveling unit to move the robot cleaner;
   an ultrasonic sensor to emit an oscillation wave, to receive a reflection wave reflected from an object surface, and to output vibration generated by the oscillation wave and vibration generated by the reception of the reflection wave as an electrical signal; and
   a controller to determine information about the object surface based on the electrical signal output from the ultrasonic sensor, and to control movement of the traveling unit based on the information about the object surface, wherein the electrical signal is an electrical signal of a composite wave appearing when the oscillation wave overlaps the reflection wave, or an electrical signal of a composite wave appearing when an aftershock generated by inertia of the oscillation wave overlaps the reflection wave, the controller calculates an average amplitude of the composite wave based on the electrical signal of the composite wave, and determines the information about the object surface based on the average amplitude of the composite wave, and the controller calculates at least one of a tail length which is a signal having a value smaller than the average amplitude in the electrical signal and an average deviation of the composite wave, and determines the information about the object surface based on the at least one of the tail length and the average deviation.

2. The robot cleaner according to claim 1, further comprising a waveform analyzer to calculate a waveform length of the composite wave based on the electrical signal of the composite wave, wherein the controller compares the waveform length of the composite wave to a reference waveform length to determine the information about the object surface.

3. The robot cleaner according to claim 1, further comprising an Analog-to-Digital (AD) converter converting the electrical signal of the composite wave into a digital signal, wherein the controller calculates the average amplitude of the composite wave using the digital signal.

4. The robot cleaner according to claim 1, wherein the controller controls a cleaning mode based on the information about the object surface.

5. The robot cleaner according to claim 1, wherein the information about the object surface includes one or more of information about a material of the object, information about whether or not the object has been contaminated, and information about whether or not an empty space exists, and wherein if it is determined that the material of the object is a soft material, that the object has been contaminated, or that an empty space exists, the controller controls avoidance traveling.

6. The robot cleaner according to claim 1, wherein the ultrasonic sensor has a closed structure.

7. The robot cleaner according to claim 1, further comprising a waveform analyzer to detect and analyze at least one wave among an oscillation wave, a reflection wave, and an echo wave from the electrical signal, wherein the controller determines the information about the object surface based on information about the at least one wave among the oscillation wave, the reflection wave, and the echo wave.

8. The robot cleaner according to claim 7, wherein the controller determines the information about the object surface based on an intensity of the reflection wave.

9. The robot cleaner according to claim 7, wherein the controller determines the information about the object surface based on a number of echo waves.

10. The robot cleaner according to claim 7, wherein the waveform analyzer detects a first attenuation rate between the reflection wave and the echo wave and a second attenuation rate between a plurality of echo waves, and wherein the controller determines the information about the object surface based on at least one attenuation rate of the first attenuation rate and the second attenuation rate.

11. A robot cleaner comprising:

a traveling unit to move the robot cleaner;

an ultrasonic sensor to emit an oscillation wave, to receive a reflection wave reflected from an object surface, and to output vibration generated by the oscillation wave and vibration generated by the reception of the reflection wave as an electrical signal;

a controller to determine information about the object surface based on the electrical signal output from the ultrasonic sensor, and to control movement of the traveling unit based on the information about the object surface and information from another ultrasonic sensor, wherein the electrical signal is an electrical signal of a composite wave appearing when the oscillation wave overlaps the reflection wave, or an electrical signal of a composite wave appearing when an aftershock generated by inertia of the oscillation wave overlaps the reflection wave, the ultrasonic sensor and the other ultrasonic sensor are disposed at different distances from the object surface to respectively detect composite waves in which different kinds of interferences occur when another reflection wave is reflected from an object surface made of the same material as the object surface;

a waveform analyzer to calculate a first waveform length of a first electrical signal output from the ultrasonic sensor, and a second waveform length of a second electrical signal output from the other ultrasonic sensor, and to analyze a first kind of interference of the composite wave in the first electrical signal and a second kind of interference of the composite wave in the second electrical signal, and the controller determines the information about the object surface based on the first waveform length and the second waveform length, and a material of the object surface based on the first kind of interference and the second kind of interference.

12. A robot cleaner comprising:

a traveling unit to move the robot cleaner;

an ultrasonic sensor to emit an oscillation wave, to receive a reflection wave reflected from an object surface, and to output vibration generated by the oscillation wave and vibration generated by the reception of the reflection wave as an electrical signal;

a controller to determine information about the object surface based on the electrical signal output from the ultrasonic sensor, and to control movement of the traveling unit based on the information about the object surface; and a waveform analyzer to detect and analyze feature points from the electrical signal of the composite wave, wherein the electrical signal is an electrical signal of a composite wave appearing when the oscillation wave overlaps the reflection wave, or an electrical signal of a composite wave appearing when an aftershock generated by inertia of the oscillation wave overlaps the reflection wave, the controller determines the information about the object surface based on the result of the analysis of the feature points, and the feature points correspond to a first time at which the composite wave starts to attenuate and a second time at which the attenuation of the composite wave terminates.

13. The robot cleaner according to claim 12, wherein the waveform analyzer further detects a gradient at which the composite wave attenuates between the first time and the second time, and wherein the controller determines the information about the object surface based on at least one of the first time, the second time, and the gradient.

14. The robot cleaner according to claim 12, wherein the waveform analyzer further detects a maintenance time period from a time at which the reflection wave is received to the first time, and
wherein the controller determines the information about the object surface based on the maintenance time period.

15. The robot cleaner according to claim 12, wherein the information about the object surface includes information about a hardness of the object surface and whether the object surface has been contaminated, and
wherein if it is determined that the object surface is soft or that the object surface has been contaminated, the controller controls avoidance traveling.

16. The robot cleaner according to claim 12, wherein the waveform analyzer detects a type of interference of the composite wave, and
wherein the controller determines whether the type of interference of the detected composite wave is a constructive interference or a destructive interference to determine whether a material of the object surface is a hard material or a soft material.

17. A method of controlling a robot cleaner, the method comprising:
driving an ultrasonic sensor to emit an oscillation wave;
receiving a reflection wave reflected from an object surface by way of the ultrasonic sensor;
detecting an electrical signal when vibration generated by the oscillation wave and vibration generated by the reflection wave are output as the electrical signal from the ultrasonic sensor;
determining information about the object surface based on the detected electrical signal; and
controlling movement of a traveling unit of the robot cleaner based on the information about the object surface,
wherein the electrical signal is an electrical signal of a composite wave appearing when the oscillation wave overlaps the reflection wave, or an electrical signal of a composite wave appearing when an aftershock generated by inertia of the oscillation wave overlaps the reflection wave,
the determining of the information about the object surface based on the electrical signal comprises:
converting the electrical signal into a digital signal;
calculating an average amplitude of each of the oscillation wave, the composite wave, and a reflection wave reflected from the object surface using the digital signal;
comparing the average amplitude to reference average amplitudes according to pre-stored information about various object surfaces to determine the information about the object surface;
calculating a tail length, which is a signal having a value smaller than the average amplitude; and
searching for a reference tail length range to which the detected tail length belongs in a plurality of reference tail length ranges according to the pre-stored information about the object surface, and determining a material of the object surface, whether the object surface has been contaminated, and whether an empty space exists.

18. A method of controlling a robot cleaner, the method comprising:
driving an ultrasonic sensor to emit an oscillation wave;
receiving a reflection wave reflected from an object surface by way of the ultrasonic sensor:
detecting an electrical signal when vibration generated by the oscillation wave and vibration generated by the reflection wave are output as the electrical signal from the ultrasonic sensor;
determining information about the object surface based on the detected electrical signal; and
controlling movement of a traveling unit of the robot cleaner based on the information about the object surface,
wherein the electrical signal is an electrical signal of a composite wave appearing when the oscillation wave overlaps the reflection wave, or an electrical signal of a composite wave appearing when an aftershock generated by inertia of the oscillation wave overlaps the reflection wave, and
the determining of the information about the object surface based on the electrical signal comprises:
converting the electrical signal into a digital signal;
calculating an average amplitude of each of the oscillation wave, the composite wave, and the reflection wave using the digital signal;
comparing the average amplitude to reference average amplitudes according to pre-stored information about various object surfaces to determine the information about the object surface;
calculating an average deviation of the composite wave using the average amplitude; and
searching for a reference average deviation range to which the detected average deviation belongs in a plurality of reference average deviation ranges according to the pre-stored information about the object surface, and determining a material of the object surface, whether the object surface has been contaminated, and whether an empty space exists.

19. The method according to claim 17, wherein the controlling of the movement of the traveling unit comprises controlling avoidance traveling if it is determined that a material of the object surface is a soft material, that the object has been contaminated, or that an empty space exists.

20. A method of controlling a robot cleaner, the method comprising:
driving an ultrasonic sensor to emit an oscillation wave;
receiving a reflection wave reflected from an object surface by way of the ultrasonic sensor;
detecting an electrical signal when vibration generated by the oscillation wave and vibration generated by the reflection wave are output as the electrical signal from the ultrasonic sensor;
determining information about the object surface based on the detected electrical signal; and
controlling movement of a traveling unit of the robot cleaner based on the information about the object surface
wherein the electrical signal is an electrical signal of a composite wave appearing when the oscillation wave overlaps the reflection wave, or an electrical signal of a composite wave appearing when an aftershock generated by inertia of the oscillation wave overlaps the reflection wave, and
the determining of the information about the object surface based on the electrical signal comprises:

detecting a first time at which the electrical signal starts to attenuate and a second time at which the attenuation of the electrical signal terminates, as feature points; and comparing the detected feature points to a plurality of reference feature points according to pre-stored information about an object surface to determine the information about the object surface.

21. The method according to claim 20, wherein the determining of the information about the object surface based on the electrical signal further comprises:

detecting a gradient at which the electric signal attenuates between the first and second times, and a maintenance time period between a time at which the reflection wave is received and the first time; and determining the information about the object surface based on at least one of the first time, the second time, the gradient, and the maintenance time period.

22. A method of controlling a robot cleaner, the method comprising:

driving an ultrasonic sensor to emit an oscillation wave;

receiving a reflection wave reflected from an object surface by way of the ultrasonic sensor;

detecting an electrical signal when vibration generated by the oscillation wave and vibration generated by the reflection wave are output as the electrical signal from the ultrasonic sensor;

determining information about the object surface based on the detected electrical signal; and controlling movement of a traveling unit of the robot cleaner based on the information about the object surface wherein the electrical signal is an electrical signal of a composite wave appearing when the oscillation wave overlaps the reflection wave, or an electrical signal of a composite wave appearing when an aftershock generated by inertia of the oscillation wave overlaps the reflection wave, and the determining of the information about the object surface based on the electrical signal comprises:

detecting a type of interference of the composite wave in the electrical signal; and determining whether the type of interference of the detected composite wave is a constructive interference or a destructive interference to determine whether a material of the object surface is a hard material or a soft material.

23. The method according to claim 22, wherein the determining of the information about the object surface based on the electrical signal comprises:

detecting an intensity of a reflection wave in the electrical signal; and comparing the intensity of the reflection wave to a plurality of reference intensities according to pre-stored information about an object surface to determine the information about the object surface.

24. The method according to claim 22, wherein the determining of the information about the object surface based on the electrical signal further comprises:

detecting a number of echo waves in the electrical signal; and comparing the detected number of echo waves to a plurality of reference numbers of echo waves according to pre-stored information about an object surface to determine a material of the object surface.

25. A method of controlling a robot cleaner, the method comprising:

driving an ultrasonic sensor to emit an oscillation wave;

receiving a reflection wave reflected from an object surface by way of the ultrasonic sensor;

detecting an electrical signal when vibration generated by the oscillation wave and vibration generated by the reflection wave are output as the electrical signal from the ultrasonic sensor;

determining information about the object surface based on the detected electrical signal; and controlling movement of a traveling unit of the robot cleaner based on the information about the object surface, wherein the electrical signal is an electrical signal of a composite wave appearing when the oscillation wave overlaps the reflection wave, or an electrical signal of a composite wave appearing when an aftershock generated by inertia of the oscillation wave overlaps the reflection wave, and the detecting of the electrical signal comprises:

emitting the oscillation wave, and receiving the oscillation wave and the composite wave, respectively, using a first ultrasonic sensor and a second ultrasonic sensor having different distances to the object surface;

detecting a first electrical signal for the oscillation wave, the reflection wave, and the composite wave using the first ultrasonic sensor; and detecting a second electrical signal for the oscillation wave, the reflection wave, and the composite wave using the second ultrasonic sensor, the determining information about the object surface comprises:

calculating a first waveform length of the first electrical signal;

calculating a second waveform length of the second electrical signal;

comparing the first waveform length to the second waveform length to select a longer waveform length from among the first and second waveform lengths; and comparing the selected waveform length to a reference waveform length to determine the information about the object surface.

26. The method according to claim 25, further comprising:

calculating a first waveform length of the first electrical signal;

calculating a second waveform length of the second electrical signal;

calculating a length difference between the first waveform length and the second waveform length; and comparing the calculated length difference to a reference waveform length value to determine the information about the object surface.

* * * * *